(12) United States Patent
Hahn et al.

(10) Patent No.: US 9,017,941 B2
(45) Date of Patent: Apr. 28, 2015

(54) MICROCHIP FOR ANALYZING NUCLEIC ACID AND METHOD OF NUCLEIC ACID ANALYSIS USING THE SAME

(71) Applicant: Postech Academy-Industry Foundation, Pohang-si (KR)

(72) Inventors: Jong Hoon Hahn, Seoul (KR); Byoung Joo Kwak, Pohang-si (KR); Han-Ok Kim, Pohang-si (KR)

(73) Assignee: Postech Academy-Industry Foundation, Pohangsi (KR)

( * ) Notice: Subject to any disclaimer, the term of this patent is extended or adjusted under 35 U.S.C. 154(b) by 100 days.

(21) Appl. No.: 13/787,968

(22) Filed: Mar. 7, 2013

(65) Prior Publication Data

US 2013/0341189 A1    Dec. 26, 2013

(30) Foreign Application Priority Data

Jun. 22, 2012    (KR) .................. 10-2012-0067568

(51) Int. Cl.
| | |
|---|---|
| C12Q 1/68 | (2006.01) |
| C12P 19/34 | (2006.01) |
| C12M 1/34 | (2006.01) |
| B66D 3/08 | (2006.01) |
| G01N 15/06 | (2006.01) |
| G01N 21/00 | (2006.01) |
| G01N 27/447 | (2006.01) |

(52) U.S. Cl.
CPC .... G01N 27/44726 (2013.01); G01N 27/44791 (2013.01); G01N 27/44743 (2013.01)

(58) Field of Classification Search
CPC ................................ G01N 27/447; C12Q 1/68
USPC ............ 435/6.1, 91.2, 287.2, 288.5; 254/400, 254/452, 455, 456, 600; 422/50, 68.1, 422/82.05
See application file for complete search history.

(56) References Cited

U.S. PATENT DOCUMENTS

| 6,887,668 B2 * | 5/2005 | Liu et al. ...................... 435/6.11 |
| 7,169,277 B2 * | 1/2007 | Ausserer et al. .............. 204/453 |
| 2007/0117092 A1 | 5/2007 | Sadarangani et al. |
| 2009/0035770 A1 * | 2/2009 | Mathies et al. ................... 435/6 |

FOREIGN PATENT DOCUMENTS

KR    1004531000000    4/2000

OTHER PUBLICATIONS

Han-Ok Kim, et al., "Compact Continuous-Flow PCR System and On-Line DNA Analysis", PITTICON 2012 Technical Program, Orlando, (Mar. 11, 2012).
Nokyoung Park, et al., "Cylindrical Compact Thermal-Cycling Device for Continuous-Flow Polymerase Chain Reaction", Anal. Chem. 2003, 75, 6029-6033 (Sep. 26, 2003).

* cited by examiner

*Primary Examiner* — Narayan Bhat
(74) *Attorney, Agent, or Firm* — Lexyoume IP Meister, PLLC

(57) ABSTRACT

A method for nucleic acid analysis including injecting a slight amount of nucleic acid sample for analysis, characterized in that most of a nucleic acid sample which is not used, excluding the slight amount of the nucleic acid sample which is used for analysis, can be obtained as a pure product which is not contaminated with a fluorescent material, and a microchip for analyzing nucleic acid which enables such method for nucleic acid analysis, are provided. The method for nucleic acid analysis may analyze at least two different nucleic acid samples in a continuous manner by sequentially injecting the at least two different nucleic acid samples.

27 Claims, 12 Drawing Sheets

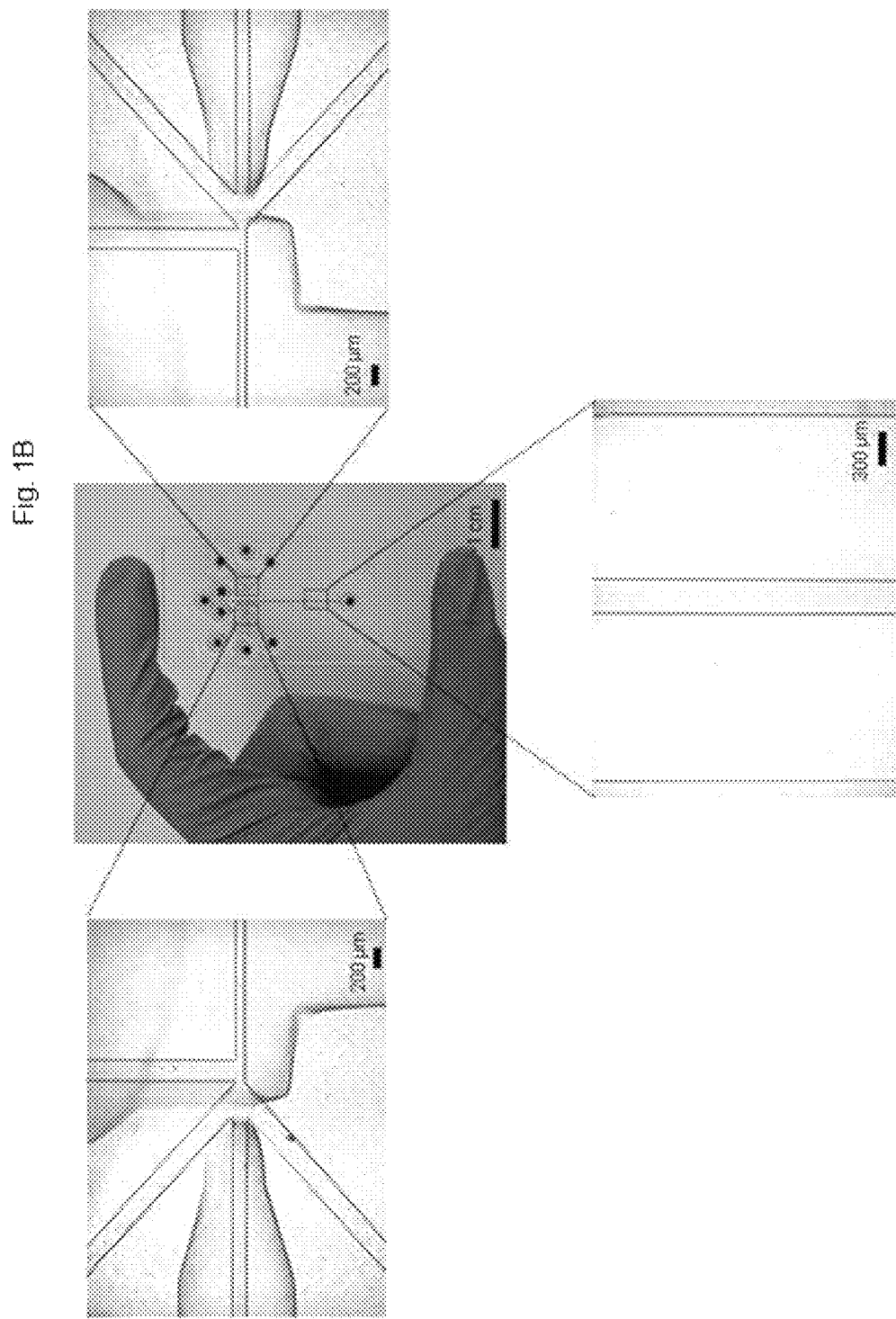

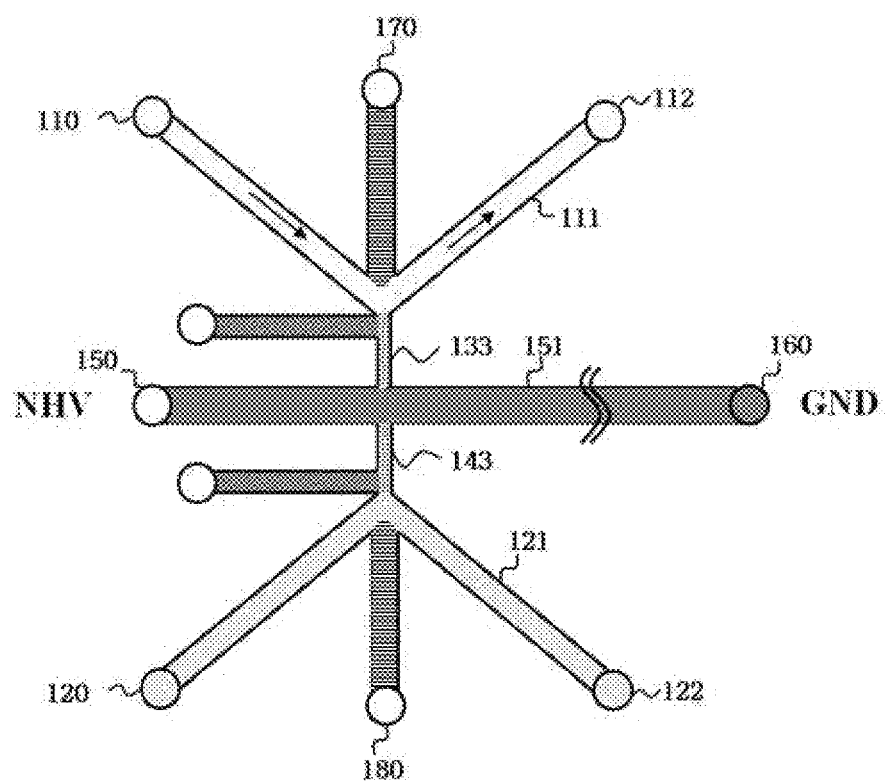

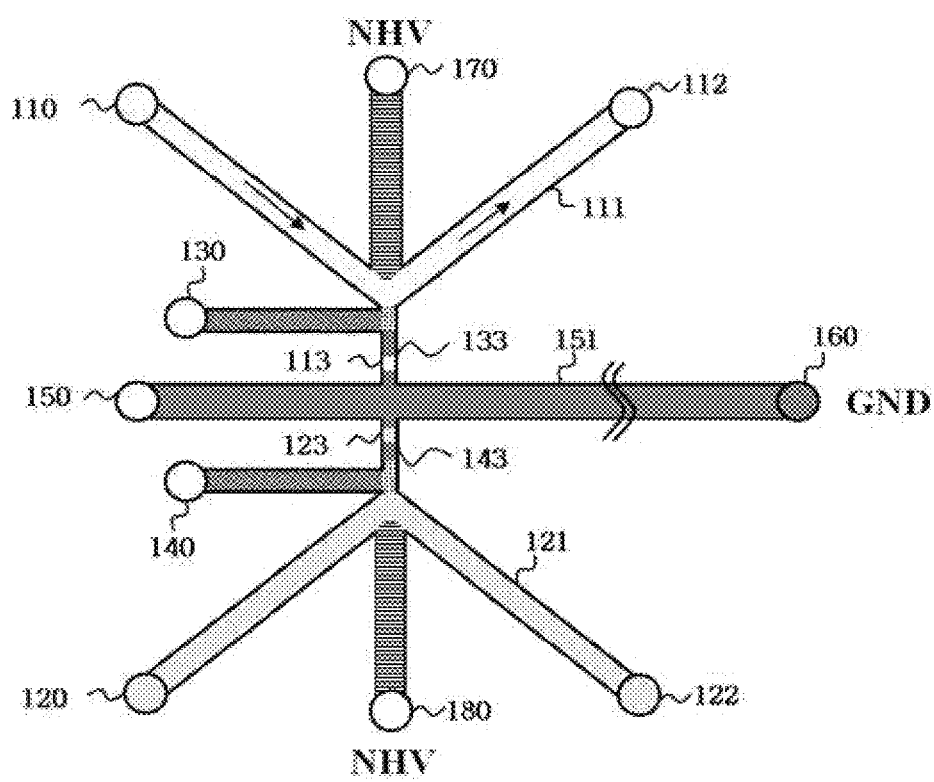

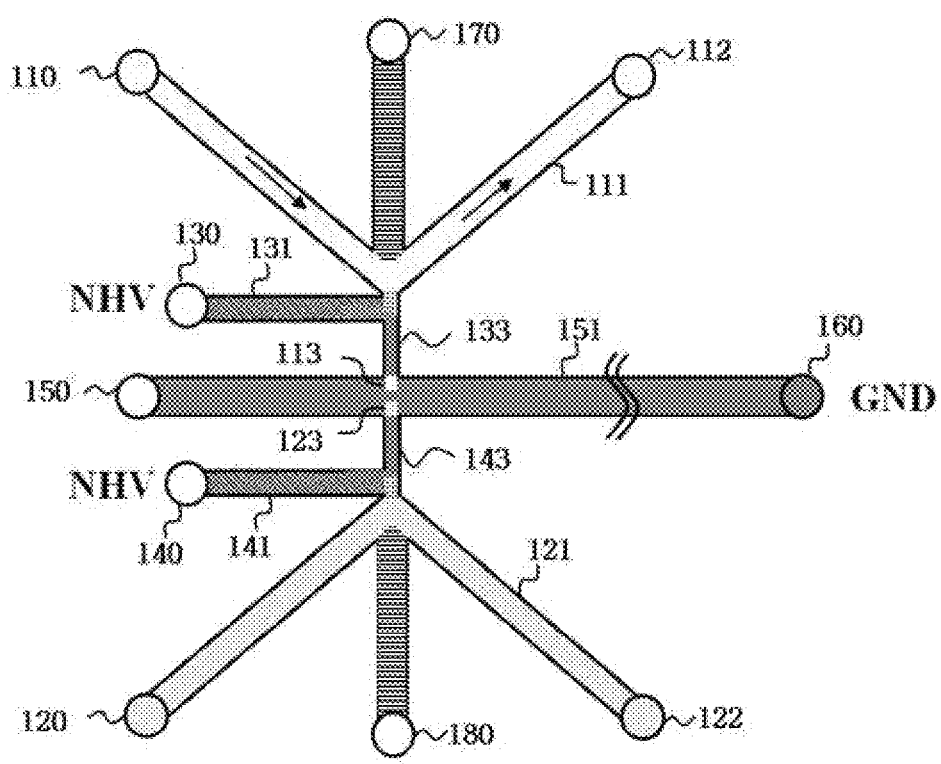

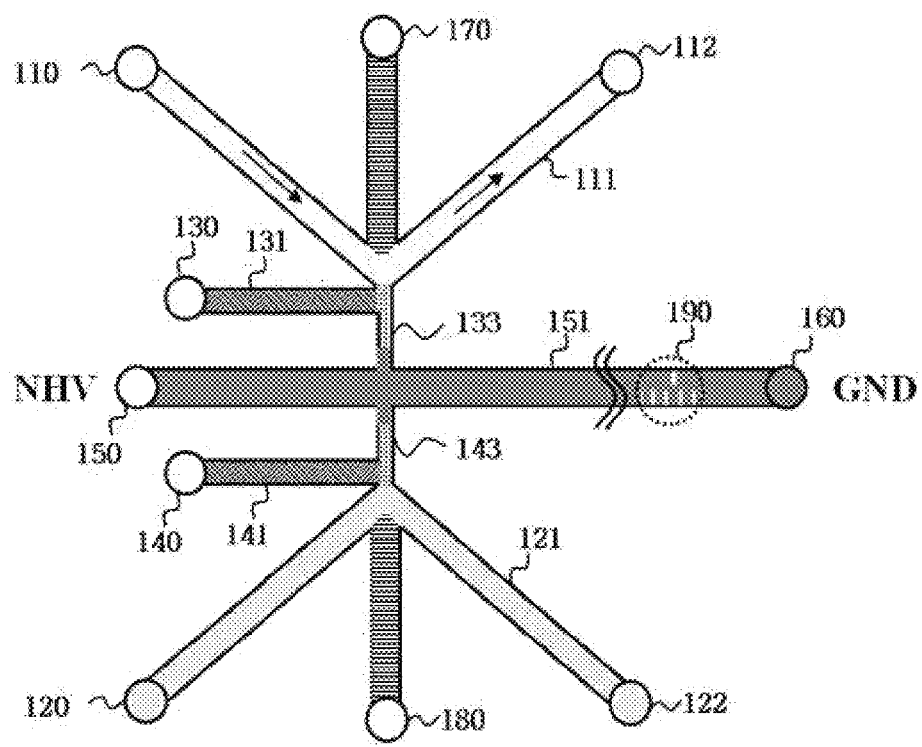

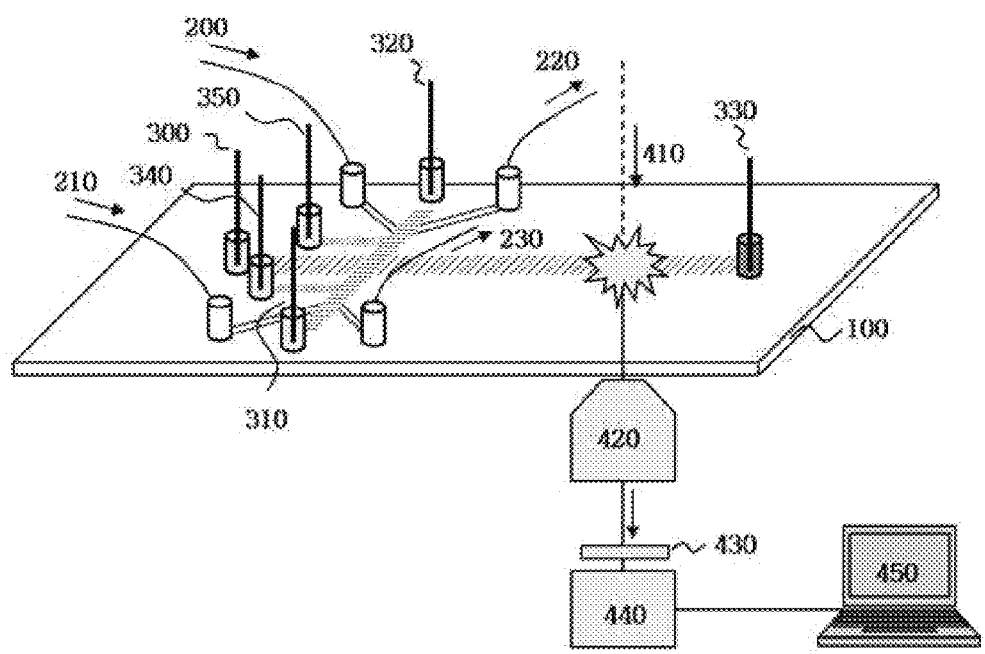

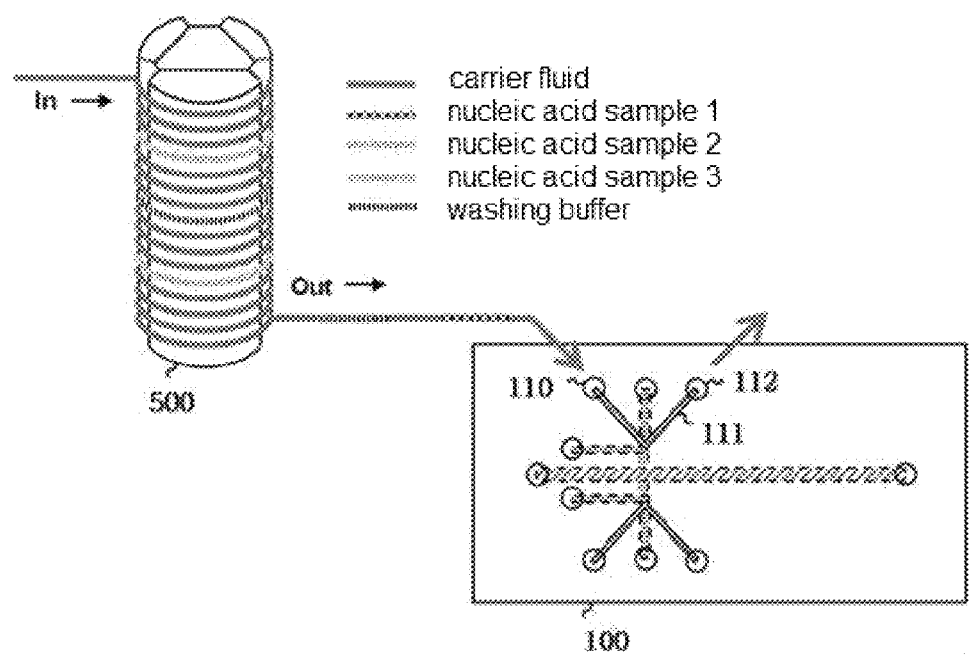

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: forward primer for 323bp DNA fragment

<400> SEQUENCE: 1
gccattctca ccggattcag tcgtc                                           25

<210> SEQ ID NO 2
<211> LENGTH: 22
<212> TYPE: DNA
<213> ORGANISM: Artificial Sequence
<220> FEATURE:
<223> OTHER INFORMATION: reverse primer for 323bp DNA fragment

<400> SEQUENCE: 2

-continued

```
agccgccgtc ccgtcaagtc ag                                              22

<210> SEQ ID NO 3
<211> LENGTH: 19
<212> TYPE: DNA
<213> ORGANISM: Artificial Sequence
<220> FEATURE:
<223> OTHER INFORMATION: forward primer for 640 bp DNA fragment

<400> SEQUENCE: 3
tccgctttcc tcctgagac                                                  19

<210> SEQ ID NO 4
<211> LENGTH: 19
<212> TYPE: DNA
<213> ORGANISM: Artificial Sequence
<220> FEATURE:
<223> OTHER INFORMATION: reverse primer for 640 bp DNA fragment

<400> SEQUENCE: 4
ggaaacactg gtcataatc                                                  19

<210> SEQ ID NO 5
<211> LENGTH: 24
<212> TYPE: DNA
<213> ORGANISM: Artificial Sequence
<220> FEATURE:
<223> OTHER INFORMATION: forward primer for 850 bp DNA fragment

<400> SEQUENCE: 5
aggctctaat gttcctaacc ctga                                            24

<210> SEQ ID NO 6
<211> LENGTH: 19
<212> TYPE: DNA
<213> ORGANISM: Artificial Sequence
<220> FEATURE:
<223> OTHER INFORMATION: reverse primer for 850 bp DNA fragment

<400> SEQUENCE: 6
tgacggttat ttcctagac                                                  19
```

MICROCHIP FOR ANALYZING NUCLEIC ACID AND METHOD OF NUCLEIC ACID ANALYSIS USING THE SAME

CROSS-REFERENCE TO RELATED APPLICATIONS

This application claims the benefit of Korean Patent Application No. 10-2012-0067568, filed on Jun. 22, 2012 with the Korean Intellectual Property Office, the disclosure of which is herein incorporated by reference in its entirety.

BACKGROUND

1) Field of the Invention

A method for nucleic acid analysis including injecting a slight amount out of nucleic acid sample, and a microchip for analyzing nucleic acid which enables such method for nucleic acid analysis, wherein, excluding the slight amount of the nucleic acid sample which is used for analysis, most of an amount of the nucleic acid sample that is not used can be obtained as a pure product which is not contaminated with a fluorescent material.

2) Background of the Invention

Nucleic acids such as DNA or RNA extracted from cells are used for diagnosis and research of diseases, but as the amounts thereof are very small, the amplification of samples is essential for analysis. Such amplification of nucleic acid samples is carried out through polymerase chain reaction (PCR), and it requires repeated temperature control between two or three temperatures, depending on the types of enzymes to be used.

Since the success of DNA amplification and the efficiency of amplification in the PCR are determined by complex factors such as temperature control of each step, the length of primers, base sequences, size of template DNA, etc., analysis procedures for identifying amplification results after PCR are essential. In general, gel electrophoresis using slab-gels such as agarose or acrylamide is employed to identify the amplification results after PCR, but it takes many steps and long time from gel manufacturing to electrophoresis and result checking, and the amplification step of samples and the analysis step thereof are separated from each other so that dilution or loss of the samples during the transfer thereof is likely to occur or it may be easily influenced by external environments.

In order to deal with this, methods of identifying PCR products after the PCR procedures on a microchip have been developed (Fu-Chun Huang et al., *Electrophoresis*, 2006, 27, 3297-3305; Isabel Rodriguez et al., *Electrophoresis*, 2003, 24, 172-178); however, as these methods allow only one PCR product to be analyzed at one time, they have a low throughput, and as the PCR products are analyzed through fluorescence detection after the reactions with fluorescent materials inside or outside the chip, purely amplified nucleic acids which are not contaminated with fluorescent materials cannot be obtained.

As described in the above, in the slab-gel mannered nucleic acid analysis using agarose or acrylamide by the prior arts, samples cannot be analyzed in a continuous manner from amplification to analysis, and further, as the samples need to be transferred to slab-gels from amplification machines, they are inevitably exposed to external environments so that there is a high contamination possibility of the samples, and the volumes of the amplified nucleic acids have to be sufficient to enable the analysis of the samples. Meanwhile, the methods for nucleic acid analysis using microchips only show the case where respective samples are amplified and then separated, and there is no case of amplified samples being separated prior to the analysis thereof in a continuous-flow manner. Therefore, they fail to accomplish high-throughput analysis, and there is also an issue that purely amplified nucleic acids which are not contaminated with fluorescent materials cannot be obtained.

SUMMARY OF THE INVENTION

Therefore, an embodiment provides a method for nucleic acid analysis using a microchip for nucleic acid analysis, including injecting a standard sample containing a standard size nucleic acid and a slight amount of a nucleic acid sample and analyzing them. The method is characterized in that most of the amount of the nucleic acid sample which is not used, excluding the slight amount of the nucleic acid sample which is used for analysis, can be obtained as a pure product not being contaminated with a fluorescent material.

In one embodiment, the method for nucleic acid analysis may be capable of analyzing at least two different nucleic acid samples in a continuous manner, by sequentially injecting the at least two different nucleic acid samples.

Another embodiment provides a microchip for analyzing nucleic acid which enables such method for nucleic acid analysis.

BRIEF DESCRIPTION OF THE DRAWINGS

FIGS. 1A and 1B show a planar view and actual photographs of a microchip for continuous nucleic acid separation and detection manufactured according to one embodiment of the invention, respectively.

FIG. 2A to FIG. 2E are operation sequence diagrams of a method for continuous nucleic acid analysis on a microchip according to one embodiment of the invention.

FIG. 3 is a structure diagram of a continuous fluorescence detection system of nucleic acid to which a microchip according to one embodiment of the invention is applied.

FIG. 5A shows a connection between a device for continuous-flow reactions and a microchip for continuous nucleic acid separation and detection according to the experiment example of the invention.

DETAILED DESCRIPTION OF THE INVENTION

Figure 1A:
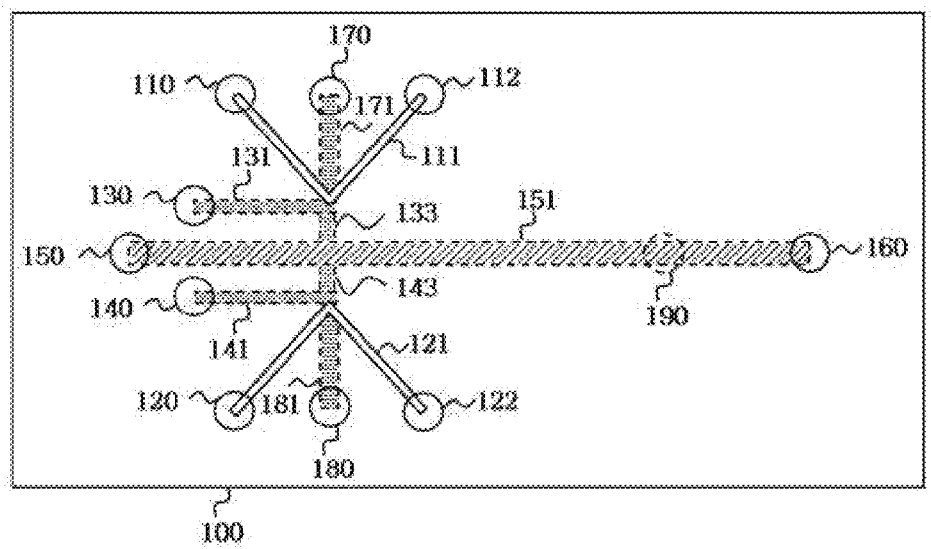

The present invention provides a method for analyzing one or more nucleic acids on a microchip, and more particularly, a method for nucleic acid analysis including introducing one or more nucleic acid samples to a microchip with microchannels formed thereon, injecting a slight amount of nucleic acid out of each introduced nucleic acid sample along with standard size nucleic acids into a separation channel part, and then separating and detecting it, and a microchip for analyzing nucleic acid capable of being used for such a method. The method may be characterized in that at least two different nucleic acid samples can be continuously analyzed; respective nucleic acid can be separated and detected by size in a continuous manner by use of only a slight amount of nucleic acid out of the nucleic acid samples so that high-throughput nucleic acid analysis can be achieved; and the nucleic acid samples which are introduced to the microchip, excluding the slight amount of the nucleic acid samples used for analysis, can be collected without being contaminated with fluorescent dyes.

The microchip for analyzing nucleic acid according to one embodiment of the invention is a microchip with microchannels formed thereon, which broadly includes an introduction channel part for the continuous flow of a nucleic acid sample and a standard sample, and a separation channel part where the separation and detection of the nucleic acid sample occur. More particularly, the microchip for analyzing nucleic acid may include:

a nucleic acid sample channel part which is connected to a nucleic acid sample supply part and a nucleic acid sample discharge part to allow continuous flow of a fluid from the nucleic acid sample supply part to the nucleic acid sample discharge part;

a standard sample channel part which is connected to a standard sample supply part and a standard sample discharge part;

a separation channel part which is located between the nucleic acid sample channel part and the standard sample channel part, one end of which a fluorescent dye storage part is connected to, and the other end of which a fluorescent dye discharge part is connected to;

a nucleic acid sample separation supplementary channel connecting the nucleic acid sample channel part and the separation channel part;

a standard sample separation supplementary channel connecting the standard sample channel part and the separation channel part;

a nucleic acid sample injection supplementary channel extended from a connection part which is a point at which the nucleic acid sample channel part and the nucleic acid sample separation supplementary channel are connected; and a standard sample injection supplementary channel extended from a connection part which is a point at which the standard sample channel part and the standard sample separation supplementary channel are connected.

An electrode may be formed at the fluorescent dye discharge part, the fluorescent dye storage part, or both of them of the separation channel part. Also, an electrode may be formed at an end of the nucleic acid sample injection supplementary channel and an end of the standard sample injection supplementary channel.

The separation channel part is connected to the nucleic acid sample channel part and the standard sample channel part, respectively through the nucleic acid sample separation supplementary channel and the standard sample separation supplementary channel; each channel is connected to the other at its connection part through which the inside of the channels is open; and the channel parts except the nucleic acid sample channel part and the standard sample channel part are all filled with a gel so that it functions as a valve for blocking the nucleic acid sample and the standard sample from traveling toward the separation channel part and the fluorescent dye of the separation channel part from traveling toward the nucleic acid sample channel part and the standard sample channel part when no voltage is applied to the microchannels. The separation channel part may be designed so that a fluorescent dye can be supplied to the separation channel part when a voltage is applied to the fluorescent sample discharge part by being either in a state of being filled with the fluorescent dye by the injection of the fluorescent dye along with the gel when the separation channel part is being formed, or being filled with the fluorescent dye by the injection of the fluorescent dye into the separation channel part filled with the gel shortly before the analysis, or by supplying the fluorescent dye to the fluorescent dye storage part while performing the analysis procedures.

In the nucleic acid sample channel part, while the nucleic acid sample supplied from the nucleic acid sample supply part is traveling toward the nucleic acid sample discharge part, only a slight amount thereof is discharged to the connection part (nucleic acid injection part) grounded with the nucleic acid sample separation supplementary channel, transferred to the separation channel, and then detected by the reaction with the fluorescent dye present in the separation channel, and the remaining most of the nucleic acid sample is collected through the discharge part in a state of not being contaminated with the fluorescent dye. In the standard sample channel part, the standard sample supplied through the standard sample supply part may be present in a state of being stored, or in a flow state, being discharged through the standard sample discharge part.

In one embodiment, the microchip for analyzing nucleic acid may be one in which the nucleic acid sample separation supplementary channel further includes a nucleic acid sample separation supplementary branch channel branched between the separation channel part and the nucleic acid sample channel part, the standard sample separation supplementary channel further includes a standard sample separation supplementary branch channel branched between the separation channel part and the standard sample channel part, the separation supplementary branch channels are each filled with a polymer gel, and an electrode is formed at an end of each of the separation supplementary branch channels.

The method for nucleic acid analysis according to one embodiment of the invention may be one using a microchip for analyzing nucleic acid with microchannels formed thereon. The microchip for analyzing nucleic acid with microchannels formed thereon may include a nucleic acid sample channel part having a nucleic acid sample supply part and a nucleic acid sample discharge part, a standard sample channel part having a standard sample supply part and a standard sample discharge part, a separation channel part including a fluorescent dye storage part at one end and a fluorescent dye discharge part at the other end thereof, a nucleic acid sample separation supplementary channel connecting the nucleic acid sample channel part and the separation channel part, and a standard sample separation supplementary channel connecting the standard sample channel part and the separation channel part, wherein the separation channel part, the nucleic acid sample separation supplementary channel, and the standard sample separation supplementary channel except the nucleic acid sample channel part and the standard sample channel part may be filled with a gel. In a preferred embodiment, the microchip for analyzing nucleic acid with microchannels formed thereon may be the microchip for analyzing nucleic acid according to the present invention described above. In the microchip, an electrode may be formed at the fluorescent dye discharge part, the fluorescent dye storage part, an end of the nucleic acid sample injection supplementary channel, and an end of the standard sample injection supplementary channel to apply a voltage.

More particularly, the method for nucleic acid analysis of the invention may include:

(1) a nucleic acid sample supply step in which a nucleic acid sample is supplied through a nucleic acid sample supply part, and the supplied nucleic acid sample flows toward a nucleic acid sample discharge part;

(2) a standard sample supply step in which standard size nucleic acids as a standard sample are supplied through a standard sample supply part;

(3) a step in which a slight amount of the nucleic acid sample which is flowing in the nucleic acid sample channel part is injected into the separation channel part through a nucleic acid sample separation supplementary channel by applying a negative voltage to an end of a nucleic acid sample injection supplementary channel extended from a connection part which is a point at which the nucleic acid sample channel part and the nucleic acid sample separation supplementary channel are connected;

(4) a step in which the standard sample is injected into the separation channel part through a standard sample separation supplementary channel by applying a negative voltage to an end of a standard sample injection supplementary channel extended from a connection part which is a point at which the standard sample channel part and the standard sample separation supplementary channel are connected;

(5) a step in which a negative voltage is applied to a fluorescent sample discharge part of the separation channel part to transfer a fluorescent dye having a positive charge to the fluorescent sample discharge part and to transfer the nucleic acid sample and the standard sample injected through the separation channel part in a direction opposite to the fluorescent sample discharge part, so that a reaction between the fluorescent dye, and the nucleic acid sample and the standard sample, occurs; and (6) a step in which the nucleic acid sample and the standard sample reacted with the fluorescent dye in the separation channel part are separated and detected by fluorescence.

The nucleic acid sample supply step and the standard sample supply step of steps (1) and (2) can be performed simultaneously or sequentially, and in any order.

In the method for nucleic acid detection and the microchip for analyzing nucleic acid according to the invention, the injection of the nucleic acid sample and/or the standard sample into the separation channel part (step (3) and step (4)) may be performed by applying a negative voltage to an end of each of the sample injection supplementary channels to transfer the nucleic acid in a direction opposite to the part to which the negative voltage is applied by the electrostatic force of repulsion. For example, the step (3) of injecting the nucleic acid sample into the separation channel part from the nucleic acid sample channel part is performed by applying the negative voltage to an end of the nucleic acid injection supplementary channel so that only nucleic acids passing through a connection part of the nucleic acid sample channel part and the nucleic acid sample separation supplementary channel, of the nucleic acids within the nucleic acid sample which are flowing in the nucleic acid sample channel part, can travel to the nucleic acid sample separation supplementary channel by the electrostatic force of repulsion when the voltage is applied.

The negative voltages to be applied during the injection of the samples in the steps (3) and (4) are in the range of −1000 V to −200 V, respectively, and they are applied for 0.1 sec. to 5 sec., particularly, about 0.1 sec. to 2 sec.

Since the nucleic acid sample is flowing in the nucleic acid sample channel part when the nucleic acid sample is injected; the area of a connection part of the nucleic acid sample channel part and the nucleic acid sample separation supplementary channel is as small as the sectional area of the nucleic acid sample separation supplementary channel; the nucleic acid sample separation supplementary channel is filled with a gel so that resistance is huge when the nucleic acid is injected; and the time for which the negative voltage is applied is short, the amount of the nucleic acids traveling to the nucleic acid sample separation supplementary channel is very slight when the flow rate of the nucleic acid sample, the area of the connection part, the resistance of the gel, and the negative voltage-applied time are considered. Accordingly, only a slight amount of the nucleic acid sample is used for analysis, and the remainder can be collected through the nucleic acid sample discharge part in a state of not being contaminated with the fluorescent dye. Further, in order to minimize the area of the connection part of the nucleic acid sample channel part and the nucleic acid sample separation supplementary channel, the nucleic acid sample channel part can be designed to be bent in such a way that an acute angle part thereof can be a point of contact with the nucleic acid sample separation supplementary channel (see FIG. 1A).

Furthermore, in order to prevent the fluorescent dye having a positive charge and located at the separation channel part by the electrostatic force of attraction by the negative voltage applied when the sample is injected in the steps (3) and (4) from traveling to the nucleic acid sample channel part or the standard sample channel part to contaminate the samples, the nucleic acid sample separation supplementary channel and the standard sample separation supplementary channel functions as a neutral zone by being located to keep the fluorescent dye exiting from the separation channel from reaching the nucleic acid sample channel part and the standard sample channel part.

In order to efficiently block the fluorescent dye from flowing into the nucleic acid sample channel part or the standard sample channel part, the nucleic acid sample separation supplementary channel may further include a nucleic acid sample separation supplementary branch channel branched between the separation channel part and the nucleic acid sample channel part, while the standard sample separation supplementary channel may further include a standard sample separation supplementary branch channel branched between the separation channel and the standard sample channel part, and an electrode may be formed at an end of each of the separation supplementary branch channels. In this structure, as the fluorescent dye having a positive charge exiting from the separation channel part to the nucleic acid sample separation supplementary channel or the standard sample separation supplementary channel travels to the negative voltage-applied part at the end of each separation supplementary branch channel by the electrostatic force of attraction when the negative voltage is applied, it can completely block the fluorescent dye from contaminating the nucleic acid sample channel part or the standard sample channel part. When the separation supplementary branch channels are present, they are also filled with a gel.

More particularly, in order to completely block the fluorescent dye from flowing into the nucleic acid sample channel part, the method of the invention may further include a step (3-1) of eliminating the fluorescent dye exiting from the separation channel part to the nucleic acid sample separation supplementary channel by applying a negative voltage to the end of the nucleic acid sample separation supplementary branch channel, in addition to the step of injecting a slight amount of the nucleic acid sample which is flowing in the nucleic acid sample part into the separation channel through the nucleic acid sample separation supplementary channel by applying a negative voltage to an end of the nucleic acid sample injection supplementary channel in the step (3). The step (3-1) may be performed simultaneously with the step (3) or subsequently thereto, and preferably, it may be performed after the application of the negative voltage for the injection of the nucleic acid sample into the end of the nucleic acid sample injection supplementary channel in step (3) is complete.

Likewise, in order to completely block the fluorescent dye from flowing into the standard sample channel part, the method of the invention may further include a step (4-1) of eliminating the fluorescent dye exiting from the separation channel part to the standard sample separation supplementary channel by applying a negative voltage to the end of the standard sample separation supplementary branch channel, in addition to the step of injecting the standard sample into the separation channel through the standard sample separation supplementary channel by applying a negative voltage to an end of the standard sample injection supplementary channel in the step (4). The step (4-1) may be performed simultaneously with the step (4) or subsequently thereto, and preferably, it may be performed after the application of the negative voltage for the injection of the standard sample into the end of the standard sample injection supplementary channel in step (4) is complete.

The negative voltages to be applied to the end of each of the separation supplementary branch channel in the steps (3-1) and/or (4-1) can be in the range of −500 V to −50 V, and the time for which the voltage is applied can be about 30 sec. to 180 sec.

In a preferred embodiment of the invention, the steps (3) and (4) of transferring the samples to the separation channel part may be performed simultaneously, that is, the slight amount of nucleic acid of the nucleic acid sample and the standard size nucleic acids of the standard sample may be injected into the separation channel part at the same time.

The negative voltage to be applied to the fluorescent sample discharge part in the step (5) can be in the range of −500 V to −50 V, and the time for which the voltage is applied can be in the range of 30 sec. to 5 min.

In step (5), the fluorescent dye exiting to each of the sample separation supplementary channels in the steps (3) and (4) and/or the remaining fluorescent dye which is not yet eliminated in steps (3-1) and (4-1) is transferred toward the separation channel part by the electrostatic force of attraction by applying a negative voltage to the fluorescent sample discharge part.

The step of detecting fluorescence from the nucleic acid sample and the standard sample reacted with the fluorescent dye in the separation channel part in the step (6) may be a step of determining the size of the sample of nucleic acids by comparing with the standard sample size of nucleic acids. In the present invention, since it is possible to perform the sample separation and fluorescence detection of the step (6) during the transfer of the samples in step (5) as well as after the fluorescence reaction of step (5), the sample separation and fluorescence detection of the step (6) may be performed simultaneously with the fluorescence reaction of step (5) or subsequently thereto.

As described above, the nucleic acid sample channel part and optionally the standard sample channel part may be those allowing continuous flow of a fluid from the sample supply part to the sample discharge part.

In the microchip for analyzing nucleic acid or the method for nucleic acid analysis of the invention, buffer solution storage parts for sample injection can be each located in the electrode region to which the negative voltage is applied at an end of the nucleic acid sample injection supplementary channel and the standard sample injection supplementary channel, and buffer solution storage parts for sample separation can be each located in the electrode region to which the negative voltage is applied at an end of the nucleic acid sample separation supplementary branch channel and the standard sample separation supplementary branch channel.

The method for nucleic acid analysis of the invention can precede a step of preparing the separation channel part including a fluorescent dye having a positive charge prior to the nucleic acid sample supply step (1) and the standard sample supply step (2), or prior to the injection step (3) of the slight amount of nucleic acid of the nucleic acid sample into the separation channel part and the injection step (4) of the standard sample into the separation channel part, by performing the following steps:

(a) a step of applying a negative voltage to the fluorescent dye discharge part of the separation channel part;

(b) a step of floating the buffer solution storage part for sample injection, the buffer solution storage part for sample separation, or the fluorescent dye discharge part; and (c) a step of grounding the fluorescent dye storage part to run a fluorescent dye or buffer solution in advance for 5 min. to 90 min.

The steps (3) and (4) of injecting the slight amount of nucleic acids of the nucleic acid sample and the standard size nucleic acid from the nucleic acid sample channel part and the standard sample channel part into the separation channel part may include:

i) a step of applying a negative voltage to the buffer solution storage part for nucleic acid sample injection and the buffer solution storage part for standard sample injection at the same time;

ii) a step of floating the buffer solution storage part for nucleic acid sample separation, the buffer solution storage part for standard sample separation, and the fluorescent dye discharge part; and iii) a step of grounding the fluorescent dye storage part.

Also, step (3-1) and step (4-1) may include, subsequently to the steps (i) and (iii):

a step of applying a negative voltage to the buffer solution storage part for nucleic acid sample separation and the buffer solution storage part for standard sample separation at the same time;

a step of floating the buffer solution storage part for nucleic acid sample injection, the buffer solution storage part for standard sample injection, and the fluorescent dye discharge part; and a step of grounding the fluorescent dye storage part.

As the method for nucleic acid analysis of the invention only uses a slight amount of the nucleic acid sample, for example, a product of nucleic acid amplification, for the analysis thereof, the remaining nucleic acid sample which is not used for the analysis can be collected in a state of not being contaminated with the fluorescent dye and thus is easily used for next step applications.

The standard size nucleic acids used as the standard sample in the invention refer to one or more nucleic acids having a size within the ranges including the size of a target nucleic acid to be analyzed, and the size thereof can be suitably determined by the size of the nucleic acid to be analyzed. For example, the standard size nucleic acids may be DNA or RNA in the range of 50 bp to 10 kbp, of one kind or at least two kinds having different sizes within the above range, for example DNA or RNA of 2 to 10 kinds, and preferably DNA.

The nucleic acid sample to be used as an analysis target in the invention may be all types of nucleic acids including deoxyribonucleic acid (DNA), ribonucleic acid (RNA), and complimentary DNA (cDNA), and particularly, it may be a product of nucleic acid amplified by PCR, etc.

The slight amount of the nucleic acid sample used for analysis refers to a range to be represented in a unit of picoliter (pL) to nanoliter (nL), and for example, it may be an amount in the range of 0.1 pL to 10 mL. Such amounts of analysis are very slight, considering that the amount of nucleic acids used in the ordinary methods for nucleic acid analysis is 1 to 10 microliters (μL), for example, 2 to 6 μL, and in this regard, the invention is characterized in that excellent analysis effects can be achieved by such use of a slight amount of nucleic acid sample.

In the method for nucleic acid analysis of the invention, the step of separating and detecting by fluorescence the slight amount of the nucleic acid sample and the standard sample injected into the separation channel part at the same time may include:

a step of applying a negative voltage to the fluorescent dye discharge part;

a step of floating the buffer solution storage part for sample injection, the buffer solution storage part for sample separation, or the fluorescent dye discharge part; and a step of grounding the fluorescent dye storage part.

Also, the step of separating the slight amount of the nucleic acid sample and the standard sample injected in the separation channel part and detecting fluorescence therefrom at the same time may detect a fluorescence signal by connecting a light source for inducing fluorescence at a part near to the fluorescent dye storage part of the separation channel part, a detector for detecting fluorescence, and an optical device for collecting the generated fluorescence to the detector. The light source may be all types of light sources capable of inducing fluorescence, and for example, it may be one or more selected from the group consisting of a light emitting device, a laser, a UV lamp, etc.

The fluorescent dye having an opposite charge (positive charge) of the nucleic acid used in the invention may be one or more selected from the group consisting of intercalating dyes which specifically bind to double-stranded nucleic acids to emit fluorescence and show a positive charge, and other fluorescent dyes having a positive charge. In particular, the intercalating dyes may be one or more selected from the group consisting of EtBr, POPO, SYBR Green, Pico Green, YOYO, and TOTO, and for example, they may be one or more selected from the group consisting of EtBr (ethidium bromide, 3,8-diamino-1-ethyl-6-phenylphenantridinium bromide, $C_{21}H_{20}BrN_3$), POPO-1 (benzoxazolium, 2,2'-[1,3-propanediylbis[(dimethyliminio)-3,1-propanediyl-1 (4H)-pyridinyl-4-ylidenemethylidyne]]bis[3-methyl]-, tetraiodide, $C_{41}H_{54}I_4N_6O_2$), SYBR Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine, $C_{32}H_{37}N_4S^+$), YOYO-1 (3-[dimethyl-[3-[4-[(Z)-(3-methyl-1,3-benzoxazol-2-ylidene)methyl]quinolin-1-ium-1-yl]propyl]azaniumyl]propyl-dimethyl-[3-[4-[(Z)-(3-methyl-1,3-benzoxazol-2-ylidene)methyl]quinolin-1-ium-1-yl]propyl] azanium tetraiodide, $C_{49}H_{58}I_4N_6O_2$), YOYO-3 ([7-dimethylazaniumylidene-1,9-bis[4-[(E,3E)-3-(3-methyl-1,3-benzoxazol-2-ylidene)prop-1-enyl]quinolin-1-ium-1-yl] nonan-3-ylidene]-dimethylazanium tetraiodide, $C_{53}H_{58}I_4N_6O_2$), and TOTO-1 (3-[dimethyl-[3-[4-[(Z)-(3-methyl-1,3-benzothiazol-2-ylidene)methyl]quinolin-1-ium-1-yl]propyl]azaniumyl]propyl-dimethyl-[3-[4-[(Z)-(3-methyl-1,3-benzothiazol-2-ylidene)methyl]quinolin-1-ium-1-yl]propyl]azanium tetraiodide, $C_{49}H_{58}I_4N_6S_2$), and the other fluorescent dyes having a positive charge may be one or more selected from the group consisting of DAPI (2-(4-carbamimidoylphenyl)-1H-indole-6-carboximidamide, $C_{16}H_{15}N_5$), Hoechst 33258 (4-[5-[6-(4-methylpiperazin-1-yl)-1H-benzimidazol-2-yl]-1,3-dihydrobenzimidazol-2-ylidene]cyclohexa-2,5-dien-1-one, $C_{25}H_{24}N_6O$), etc., but they are not limited thereto and can be any fluorescent dyes having a positive charge to be used for nucleic acid analysis.

Another characteristic of the invention lies in that it enables at least two different nucleic acid samples to be continuously analyzed by supplying at least two (2 to 100 types, in particular, 2 to 10 types) different nucleic acid samples, for example (multiple samples), sequentially.

For this, the method for nucleic acid analysis may perform the step of supplying the nucleic acid sample to the nucleic acid sample channel part through the nucleic acid sample supply part by sequentially supplying at least two different nucleic acid samples to the nucleic acid sample channel part through the nucleic acid sample supply part. The step of sequentially introducing at least two different nucleic acid samples may be performed by being connected to a pump for sample transport containing at least two different nucleic acid samples or a continuous nucleic acid amplification device for producing at least two different amplified products to sequentially introduce the nucleic acid samples.

The at least two different nucleic acid samples introduced by being connected to the pump for sample transport or the nucleic acid amplification device may be transported to the nucleic acid sample channel part by being placed between carrier fluids which are not mixable with water, in order to have an interval between respective sample supply so that each analysis results are not overlapped with each other. For example, in case of including nucleic acid sample 1, nucleic acid sample 2, nucleic acid sample 3, . . . , nucleic acid sample n, they can be introduced to the nucleic acid sample supply part in a sequence of nucleic acid sample 1—carrier fluid—nucleic acid sample 2—carrier fluid—nucleic acid sample 3—carrier fluid —, . . . , —nucleic acid sample n.

Furthermore, in order to prevent a nucleic acid sample from remaining after the use thereof to interrupt the analysis of a subsequent, different nucleic acid sample when at least two different nucleic acid samples are used, the invention may include a step of eliminating a remaining nucleic acid sample which is previously used by additionally applying a washing solution when the carrier fluids are applied. For example, in case of including nucleic acid sample 1, nucleic acid sample 2, nucleic acid sample 3, . . . , nucleic acid sample n, they can be introduced to the nucleic acid sample supply part in a sequence of nucleic acid 1—carrier fluid—washing solution—carrier fluid—nucleic acid sample 2—carrier fluid—washing solution—carrier fluid—nucleic acid sample 3—carrier fluid—washing solution—carrier fluid, . . . , —nucleic acid sample n.

A supply interval between at least two different nucleic acid samples can be adjusted by regulating the amount and/or travel speed of the carrier fluid and/or washing solution so that the following nucleic acid sample can be supplied simultaneously with or subsequently to the separation and detection in the separation channel part.

The carrier fluid and the washing solution entering between the at least two different nucleic acid samples are injected to prevent carry-over between the samples, and in particular, the carrier fluid is hydrophobic and thus prevents respective samples and washing solution which are hydrophilic from being mixed with each other, and the washing solution serves to wash the previous sample which might remain on Teflon tubes or microchannels and indicate the location of the sample within capillary tubes when the sample continuously flows. As the washing solution, ordinary loading dyes used for gel electrophoresis such as a 6× loading buffer (30% glycerol, 30 mM EDTA, 0.03% bromophenol blue, 0.03% xylene cyanol), 6× Blue/orange loading dye (Promega; 0.4% orange G, 0.03% bromophenol blue, 0.03% xylene cyanol FF, 15% Ficoll 400, 10 mM tris-HCl (pH 7.5), and 50 mM EDTA (pH 8.0)), 5× sucrose loading dye (Fisher Scientific; 40% sucrose), etc. may be used, and as the carrier fluid, one or more selected from the group consisting of perfluorodecalin ($C_{10}F_{18}$, CAS No. 306-94-5), FC-77 (3M Fluorinert electronic liquid FC-77, $(C_8F_{18})n$, $(C_8F_{16}O)m$, CAS No. 52623-00-4) and FC-40 (3M Fluorinert electronic liquid FC-40, CAS No. 51142-49-5) which are fluorous solvents, and a mineral oil may be used.

The step of sequentially introducing at least two different nucleic acid samples may be performed by supplying one type of nucleic acid sample and performing each step mentioned in the above and then by repeatedly performing step (1) of introducing a different nucleic acid sample through the nucleic acid sample supply part and its following steps, simultaneously with or subsequently to the step (6) of separating and detecting, by fluorescence, a slight of amount of nucleic acid sample and the standard sample injected into the separation channel part (which may be performed simultaneously with or subsequently to step (5)).

The electrodes connected to the microchip for analyzing nucleic acid of the invention may be in any ordinary form of electrodes including a form of conducting wires being connected to each electrode region (buffer solution or fluorescent dye storage part and discharge part) or a form of metals being deposited on the bottom board of the microchip, and the electrodes may be made of one or more materials selected from the group consisting of gold, silver, platinum, copper, aluminum, and indium tin oxide (ITO).

As previously described, the separation channel part, the nucleic acid injection supplementary channel, the standard sample injection supplementary channel, the nucleic acid sample separation supplementary channel, and the standard sample separation supplementary channel except the nucleic acid sample channel part and the standard sample channel part may be filled with a polymer gel with a network structure. The polymer gel may be selectively gelated by light by including a photoinitiator, and for example, it may be one or more selected from the group consisting of polyacrylamide gel, agarose, hydroxyalkyl cellulose, polyvinyl alcohol, and dextran. The polymer gel is filled into the microchannels in a polymer gel solution state of a concentration of about 1 to 50% (w/v) being mixed with a buffer solution.

For example, the polyacrylamide gel may be in a form of a polymer cross-linked by bis-polyacrylamide, or a linear polymer, and the concentration thereof may be within the range of 2~6% T (the sum of the weights of acrylamide and bis-polyacrylamide with regard to the volume of the total gel solution, w/v %) and/or 3~6% C (the weight of bis-acrylamide with regard to the sum of the weights of acrylamide and bis-acrylamide, w/w %), but is not limited thereto.

As the photoinitiator used for the gelation of the polymer gel solution, one or more selected from the group consisting of riboflavin, riboflavin 5'-phosphate, ammonium persulfate, TEMED (N,N,N',N'-tetramethylethylenediamine), benzoin ether, benzophenone derivatives, 2,2-dimethoxy-1,2-diphenylethan-1-one (e.g., Irgacure® class products (754, 651, 369, 907) by Ciba Co.), etc. may be used, but is not limited thereto.

When the polymer gel solution containing the photoinitiator is irradiated with UV, gelation occurs. Accordingly, if the polymer gel solution containing the photoinitiator is filled into the microchannels, and parts to be gelated are selectively irradiated with UV while the remaining parts are shielded, only desired parts can be gelated.

For the detection of a fluorescence signal generated in the separation channel part, a light source for inducing fluorescence at a part near the fluorescent dye storage part of the separation channel part, a detector for detecting fluorescence, and an optical device for collecting the generated fluorescence to the detector may be further included. As the light source, a laser irradiating light of certain wavelengths, a light-emitting diode (LED), and a UV lamp may be used and as the detector for detecting fluorescence, and a photomultiplier tube, a diode, and a charge coupled device may also be used. The optical device may include an optical lens and a filter, and a condensing lens capable of passing through lights of certain wavelengths and adjusting the size of the lights emitting from a light source to fit the size of the microchannels, an object lens that collects fluorescent light to deliver it to the detector, and a filter for shielding light scattered from the light source and effectively detecting only fluorescence may be included.

The nucleic acid sample supply part may be connected to a pump for sample transport or a nucleic acid amplification device, and the pump for sample transport or the nucleic acid amplification device may be those which transport at least two different nucleic acid samples or produce at least two different amplified nucleic acid products by continuous nucleic acid amplification, that is, those capable of continuous analysis of at least two different nucleic acid samples.

The nucleic acid amplification device may be a device for continuous-flow reactions usefully applicable to the reaction of continuously-flowing fluids, in particular, polymerase chain reaction, such as a device for continuous-flow reactions used for reactions requiring repeated temperature control over time disclosed in KR 2005-0078568.

More particularly, the nucleic acid amplification device may include:

(1) at least two solid heating blocks controlled at different temperatures; and (2) a capillary tube having a first end for fluid inlet and a second end for fluid outlet to permit continuous flow of a fluid from the first end to the second end, wherein the capillary tube sequentially or repeatedly contacts the heating blocks controlled at different temperatures from each other.

In another example, the nucleic acid amplification device may include:

(1) at least two solid heating blocks controlled at different temperatures from each other;

(2) an insulating block contacting the heating blocks and arranged to prevent the heating blocks from being in direct contact with each other; and (3) a capillary tube which has a first end as a fluid inlet and a second end as a fluid outlet and allows continuous flow of a fluid from the first end to the second end, wherein the capillary tube is in contact with the heating blocks controlled to different temperatures from each other, sequentially or repeatedly.

Each of the heating blocks may be controlled to different temperatures from each other by a heater or a temperature sensor, the heating blocks may be made of an electrothermal material selected from the group consisting of copper, iron, aluminum, brass, gold, silver, and platinum, the insulating block may be made of a material of bakelite or an acryl polymer resin, and the capillary tube may be made of a material selected from the group consisting of glass, molten silica, polytetrafluoroethylene (PTFE), and polyethylene.

The outer wall of the capillary tube may be coated with polyimide or PTFE, and the inner wall of the capillary tube may be coated with one or more materials selected from the group consisting of trimethylchlorosilane, dimethyldichlorosilane, methyltrichlorosilane, trimethylmethoxysilane, dimethyldimethoxysilane, and methyltrimethoxysilane.

The capillary tube may be wound around the outer surface of the heating blocks, the capillary tube may be secured to spiral grooves formed on the outer surface of the heating blocks, and for example, the capillary tube may be wound 10 times to 50 times.

Also, the nucleic acid amplification device may be a device for performing PCR, which includes:

(1) three solid heating blocks which are controlled to different temperatures from one another;

(2) an insulating block which is in contact with the heating blocks and arranged to prevent each heating block from being in direct contact with one another; and (3) a capillary tube which has a first end as a PCR mixture solution inlet and a second end as a PCR product outlet and allows continuous flow of a solution from the first end to the second end, wherein the capillary tube is in contact with the three heating blocks controlled to different temperatures from one another, sequentially or repeatedly.

The nucleic acid amplification device may be a device capable of real-time reaction detection, and further includes:

(a) a fluorescence-inducing device including a light source for inducing fluorescence, a detector for detecting fluorescence, and an optical device for collecting fluorescence which is generated into the detector after the capillary tube is irradiated with light; and (b) a scanning device capable of changing a relative location of the fluorescence-inducing device and the capillary tube.

The real-time reaction may be a real-time PCR.

In another example, the nucleic acid amplification device may be a device for multiple continuous-flow reactions which is an assembly of solid heating blocks and insulating blocks, characterized in that at least two assemblies wound with a capillary tube having a first end as a fluid inlet and a second end as a fluid outlet and allowing continuous flow of a fluid from the first end to the second end are assembled to heating blocks capable of temperature control or insulating blocks to perform at least two independent reactions.

Various channels produced in the microchip for analyzing nucleic acid of the invention are those having a length and a width (breadth) in a unit of micron, which are also mentioned as microchannels in this specification. For example, the length of each channel may be 10 to 100 μm, particularly 30 to 70 μm, the width of the nucleic acid sample channel part and the standard sample channel part may be 150 to 250 μm, particularly 180 to 220 μm, the width of the nucleic acid sample injection supplementary channel, the standard sample injection supplementary channel, the nucleic acid sample separation supplementary channel, and the standard sample separation supplementary channel may be 120 to 180 μm, particularly 130 to 170 μm, and the width of the separation channel part may be 250 to 350 μm, particularly 280 to 320 μm. The distance from the sample (nucleic acid sample or standard sample) supply part to the separation channel part (half the length of the nucleic acid sample channel part or the standard sample channel part and the length of each sample separation supplementary channel) may be 8 to 20 mm, particularly 10 to 15 mm, and more particularly about 12 mm, the length of the separation supplementary channels of each sample for preventing contamination of the sample by fluorescent dye may each be 1 to 20 mm, particularly 2 to 15 mm, and more particularly 5 to 12 mm, the combined length of the separation supplementary channels and the separation supplementary branch channels of each sample may be 5 to 30 mm, particularly 10 to 15 mm, and more particularly about 13 mm, and the total length of the separation channel part may be 1 to 100 mm, particularly 10 to 50 mm or so, but are not limited thereto, and they may be suitably adjusted according to the purpose of use and form thereof. The width of each channel part may be adjusted to the width of the separation channel part >the width of the nucleic acid sample channel part and the standard sample channel part >the width of the nucleic acid sample injection supplementary channel, the standard sample injection supplementary channel, the nucleic acid sample separation supplementary channel, and the standard sample separation supplementary channel.

Briefly, effects obtained by the representatives among the disclosed embodiments in accordance with the invention are as follows.

The invention enables quality analysis capable of identifying the size of a nucleic acid sample by sequentially introducing each nucleic acid sample to a microchip and injecting it along with standard size nucleic acids to separate and detect them, and it can continuously analyze different multiple nucleic acid samples which flow sequentially as well as one nucleic acid sample, thereby enabling high-speed and high-throughput analysis operation. Furthermore, it is a method capable of obtaining the nucleic acids out of the nucleic acid sample which are introduced to the microchip but not used for analysis, without being contaminated with fluorescent dyes. This device can be used in the separation and detection system of PCR products, and its analysis is possible by being coupled with a PCR device and microchip so that it can minimize the dilution or loss of samples which might occur during the transfer procedure thereof.

Since amplified products along with the analysis of amplified nucleic acids can be obtained through the invention without being contaminated with fluorescent dyes, the invention is applicable to cloning, sequence analysis, and disease diagnosis in molecular biology research, and it can also be utilized for structure analysis of nucleic acids through linkage with a mass spectrometer.

Hereafter, the invention will be described in detail with reference to the attached drawings. In describing the invention below, if concrete description about known functions or structures is deemed to make the essentials of the invention unnecessarily unclear, detailed description thereof will be omitted. The examples are only provided for illustrative purposes, without limiting the protection scope of the invention, and various modifications are possible within a scope not departing its technical essentials.

FIG. 1A is a planar view of a microchip for continuous nucleic acid detection according to an example of the invention, and FIG. 1B is photographs of the microchip actually manufactured.

In reference to FIG. 1A, the microchip for continuous nucleic acid separation and detection (100) includes a nucleic acid sample supply part (110), a nucleic acid sample channel part (111), a nucleic acid sample discharge part (112), a standard sample supply part (120), a standard sample channel part (121), a standard sample discharge part (122), a fluorescent dye storage part (160), a separation channel part (151), a fluorescent dye discharge part (150), a buffer solution storage part for nucleic acid sample injection (170), a buffer solution storage part for standard sample injection (180), a buffer solution storage part for nucleic acid sample separation (130), a buffer solution storage part for standard sample separation (140), a nucleic acid separation supplementary channel (133), a standard sample separation supplementary channel (143), a nucleic acid separation supplementary branch channel (131), a standard sample separation supplementary branch channel (141), a nucleic acid sample injection supplementary channel (171), a standard sample injection supplementary channel (181), and a light detection part (190).

The nucleic acid sample channel part (111) can allow continuous flow of a fluid from the nucleic acid sample supply part (110) to the nucleic acid sample discharge part (112) by being connected with the nucleic acid sample discharge part (110) and the nucleic acid sample discharge part (112). The standard sample channel part (121) is connected with the standard sample supply part (120) and the standard sample discharge part (122). The separation channel part (151) is located between the nucleic acid sample channel part (111) and the standard sample channel part (121), and the fluorescent dye storage part (160) is connected to one end of the separation channel part (151) and the fluorescent dye discharge part (150) is connected to the other end of the separation channel part (151).

The nucleic acid sample separation supplementary channel (133) connects the nucleic acid sample channel part (111) and the separation channel part (151), and the standard sample separation supplementary channel (143) connects the standard sample channel part (121) and the separation channel part (151). The nucleic acid sample separation supplementary channel (133) includes the nucleic acid sample separation supplementary branch channel (131) branched between the separation channel part (151) and the nucleic acid sample channel part (111), and the standard sample separation supplementary channel (143) includes the standard sample separation supplementary branch channel (141) branched between the separation channel part (151) and the standard sample channel part (121). The nucleic acid sample injection supplementary channel (171) is extended from a connection part which is a point at which the nucleic acid sample channel part (111) is connected with the nucleic acid sample separation supplementary channel (133), and the standard sample injection part channel (181) is extended from a connection part which is a point at which the standard sample channel part (121) is connected with the standard sample separation supplementary channel (143).

All the microchannels with the exception of the nucleic acid sample channel part (111) where nucleic acids continuously flow and the standard sample channel part (121) into which the standard sample is introduced, of the microchannels of the microchip, are filled with a polymer gel. That is, the separation channel part (151), the nucleic acid sample separation supplementary channel (133), the standard sample separation supplementary channel (143), the nucleic acid sample injection supplementary channel (171), the nucleic acid separation supplementary branch channel (131), the standard sample injection supplementary channel (181), and the standard sample separation supplementary branch channel (141) are filled with the polymer gel.

Meanwhile, an electrode is formed at the fluorescent dye discharge part (150), the fluorescent dye storage part (160), an end of the nucleic acid injection supplementary channel (171), an end of the nucleic acid separation supplementary branch channel (131), an end of the standard sample injection supplementary channel (181), and an end of the standard sample separation supplementary branch channel (141).

The substrate of the microchip (100) is made of a material capable of allowing the incident light from a light source into the channels inside the chip and penetrating the fluorescence of fluorescent materials inside the channels, and can be manufactured by selecting poly(dimethylsiloxane) (PDMS), poly(methylmethacrylate (PMMA), polycarbonate (PC), polyvinylchloride (PVC), acryl, glass, etc. which are processable into a channel by the prior arts.

The microchannels of the microchip (100) can be manufactured by using any one of the methods such as photolithography, hot embossing, casting, laser ablation, mechanical processing, pressing, etc.

Also, the microchip may include a storage part in the form of a tubing to enable the storage of the samples, the connection of capillary tubes, the introduction of electrodes, etc. The storage part can be made of, but is not limited to, polymers such as silicon and Teflon, glass, and so on, and the materials can be adjusted depending on the solvent to be used.

Certain microchannels (131, 133, 141, 143, 151, 171, and 181) within the microchip are filled with gels. A polyacrylamide solution or a Reprogel 377 solution (Amersham Biosciences, USA) containing a photoinitiator can be employed to fill only certain microchannels with the gels by photo-induced gelation. Gel solutions are injected into all the microchannels through the storage parts and filled without air bubbles, and if UV is exposed to only parts to be gelated while the other parts are being blocked from UV using a mask, gels are only formed in the parts which are exposed to UV. The exposure time to UV can vary by the strength of a light source, the size of channels, and the concentration of a gel solution, and the gel solutions which remain ungelated after UV exposure are to be eliminated.

The gels within the microchannels function as a separation medium for separating samples by the size thereof using an electric field, and as a valve for controlling the injection of samples and preventing the samples and fluorescent dyes from being mixed with each other before injection.

FIG. 2 is a state diagram according to the operation sequence of the microchip for continuous nucleic acid detection by an example of the invention.

Figure 2A:
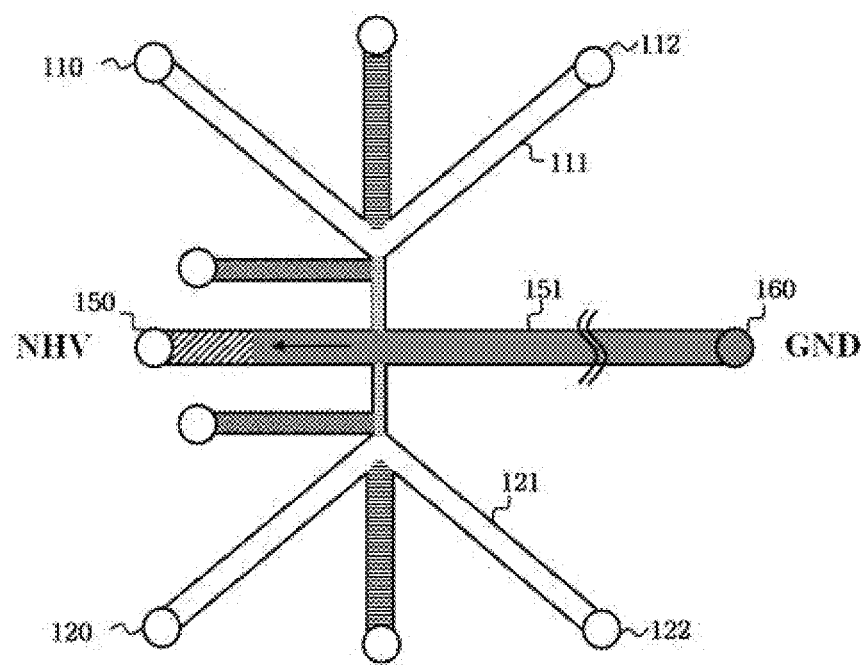

FIG. 2A shows a step of preparing for conditions for nucleic acid analysis, and when a negative voltage is applied to the fluorescent dye discharge part (150), the fluorescent dye storage part (160) is grounded (GND), and a buffer solution storage part for nucleic acid sample injection (170), a buffer solution storage part for standard sample injection (180), a buffer solution storage part for nucleic acid sample separation (130), and a buffer solution storage part for standard sample separation (140) are floated, the fluorescent dye travels toward the fluorescent dye discharge part (150) from the fluorescent dye storage part (160) through the separation channel part (151). This procedure is a step to make a condition under which a subsequent nucleic acid sample and standard sample are easily reacted with the fluorescent dye, by running the fluorescent dye in advance into the gel of the separation channel part (151). For the fluorescent dye, those having a charge to be able to move by an electric field, in particular, those having a positive charge to be easily coupled by the electrostatic force of attraction with nucleic acids which, on the contrary, have a negative charge, and being coupled with the nucleic acids at a fast reaction rate, are preferable. Also, standard size nucleic acids can become the standard sample, and in particular, in order to accurately determine the size of the nucleic acid samples, the size of the nucleic acid samples should be included within the size range of the standard size nucleic acids.

FIG. 2B shows a step of adding the standard sample to the microchip and sequentially introducing nucleic acid samples, wherein the nucleic acid samples enter through a nucleic acid sample supply part (110), pass through a nucleic acid sample channel part (111), and exit via a nucleic acid sample discharge part (112) by being connected with a syringe pump or a nucleic acid amplification device, and the standard sample is added to a standard sample supply part (120) and filled in a standard sample channel part (121) using pressure from the outside or capillary action.

FIG. 2C shows a first step of injecting a slight amount of the nucleic acid sample (113) and the standard sample (123) into the nucleic acid sample separation supplementary channel (133) and the standard sample separation supplementary channel (143) of the microchip, and when a negative voltage is applied to the buffer solution storage part for nucleic acid sample injection (170) and the buffer solution storage part for standard sample injection (180) for a short time, at the same time, the fluorescent dye storage part (160) is grounded, and the buffer solution storage part for nucleic acid sample separation (130), the buffer solution storage part for standard sample separation (140), and the fluorescent dye discharge part (150) are floated, the slight amount of the nucleic acid sample (113) which is flowing in the nucleic acid sample channel part (111) and the standard sample (123) which is filled in the standard sample channel part (121) travel toward the nucleic acid sample separation supplementary channel (133) and the standard sample separation supplementary channel (143), respectively. Meanwhile, since the fluorescent dye has a positive charge which is opposite to that of the nucleic acid, it travels toward the nucleic acid sample separation supplementary channel (133) and the standard sample separation supplementary channel (143) from the separation channel part (151) in a counter-flow opposite to the travel direction of the slight amount of the nucleic acid sample (113) and the standard sample (123).

FIG. 2D shows a second step of injecting the slight amount of the nucleic acid sample (113) and the standard sample (123) in the nucleic acid sample separation supplementary channel (133) and the standard sample separation supplementary channel (143) of the microchip, and when a negative voltage is applied to the buffer solution storage part for nucleic acid sample separation (130) and the buffer solution storage part for standard sample separation (140) at the same time, the fluorescent dye storage part (160) is grounded, and the buffer solution storage part for nucleic acid sample injection (170), the buffer solution storage part for standard sample injection (180), and the fluorescent dye discharge part (150) are floated, the slight amount of the nucleic acid sample (113) and the standard sample (123) in the nucleic acid sample separation supplementary channel (133) and the standard sample separation supplementary channel (143) travel to the separation channel part (151). Meanwhile, the fluorescent dye travels to the nucleic acid sample separation supplementary branch channel (131) and the standard sample separation supplementary branch channel (141) from the nucleic acid sample separation supplementary channel (133) and the standard sample separation supplementary channel (143) in a counter-flow which is opposite to the travel direction of the slight amount of the nucleic acid sample (113) and the standard sample (123).

FIG. 2E shows a step of separating and detecting the slight amount of the injected nucleic acid sample (113) and the standard sample (123) from the separation channel part (151) at the same time, and like FIG. 2A, when a negative voltage is applied to the fluorescent dye discharge part (150), the fluorescent dye storage part (160) is grounded, and the buffer solution storage part for nucleic acid sample injection (170), the buffer solution storage part for standard sample injection (180), the buffer solution storage part for nucleic acid sample separation (130), and the buffer solution storage part for standard sample separation (140) are floated, the slight amount of the nucleic acid sample (113) and the standard sample (123) injected into the separation channel part (151) travel toward the fluorescent dye storage part (160) and they are separated by the size thereof. The slight of the nucleic acid sample (113) and the standard sample (123) are separated from the separation channel part (151), and at the same time, they are coupled with the fluorescent dye, and when they pass through a fluorescence detection part (190), they are irradiated with light of certain wavelengths from a light source and thus enter an excitation state to emit fluorescence, which is then detected via a detector. The fluorescent dye travels to the separation channel part (151) from the nucleic acid sample separation supplementary branch channel (131), the nucleic acid sample separation supplementary channel (133), the standard sample separation supplementary branch channel (141), and the standard sample separation supplementary channel (143). Because the buffer solution storage part for nucleic acid sample injection (170), the buffer solution storage part for standard sample injection (180), the buffer solution storage part for nucleic acid sample separation (130), and the buffer solution storage part for standard sample separation (140) come to have a relatively positive charge due to the negative voltage applied to the fluorescent dye discharge part (150), the fluorescent dye having the same positive charge travels toward the separation channel part by the electrostatic force of repulsion. Hence, the step of separating and detecting the slight amount of the injected nucleic acid sample (113) and the standard sample (123) from the separation channel part (151) sends fluorescent dyes which might remain near the nucleic acid sample channel part (111) and the standard sample channel part (121) toward the separation channel part, and accordingly, in continuous sample analysis, this step serves to prevent the samples from being contaminated by the inflow of the fluorescent dyes into the nucleic acid sample channel part (111) and the standard sample channel part (121) by a counter-flow of the fluorescent dye. Thereafter, for continuous nucleic acid separation and detection, the method returns to the procedure of FIG. 2B, where nucleic acids flow to the microchip, and the procedures from FIG. 2C to FIG. 2E are performed. Since the procedure of FIG. 2A has the same voltage application step as the procedure of FIG. 2E, the procedure of FIG. 2A can also be carried out through the procedure of FIG. 2E to separate and detect different nucleic acids in a continuous manner.

FIG. 3 is a structural view of a continuous nucleic acid detection system according to an example of the invention. In particular, it includes a light source for inducing fluorescence from samples, a detector for detecting fluorescence, and an optical device for collecting the fluorescence into the detector after a separation channel is irradiated by a light source. As shown in FIG. 3, the nucleic acid detection system includes a light source part (410), a microchip for continuous nucleic acid detection (100), tubing for sample injection (200, 210), tubing for sample collection (220, 230), an optical lens (420), a filter (430), a detector (440), a data processor (450), and electrodes (300, 310, 320, 330, 340, and 350).

In reference to FIG. 3, a laser capable of irradiating the lights of certain wavelengths, an LED (light-emitting diode), or a UV lamp can be used as the light source part (410) for inducing fluorescence, and a photomultiplier tube, a diode, a charge coupled device, etc. can be used for the detector for detecting fluorescence.

The optical lens (420) and the filter (440) may include a condensing lens capable of passing the lights of certain wavelengths therethrough and adjusting the size of the lights emitting from a light source to fit the size of microchannels, an object lens that collects fluorescence light to deliver it to the detector, and a filter for shielding scattered light from the light source and effectively detecting only fluorescence.

The electrodes are connected with each storage part (130, 140, 150, 160, 170, and 180) of the microchip and serve to supply a voltage or float. As the materials of the electrodes, gold, silver, platinum, copper, aluminum, etc. are possible, and as the form of the electrodes, a form of a conducting wire or a metal such as gold and ITO being deposited on the bottom board of the microchip is possible.

EXAMPLES

Hereafter, the present invention will be described in more detail by virtue of the following examples. They are intended to merely illustrate the invention and are not construed to limit the scope of the invention in any way.

Example 1

Manufacture of Microchip for Continuous Nucleic Acid Separation—Detection

A microchip was manufactured by using a PDMS with engraved microchannels having a configuration depicted in FIG. 1 formed thereon as a top plate and using a flat glass as a bottom plate, and then integrating them to each other. The depth of each microchannel was equally 50 µm, and the widths were 200 µm in case of the nucleic acid sample channel part (111) and the standard sample channel part (121), 150 µm in case of the nucleic acid sample injection supplementary channel (171), the standard sample injection supplementary channel (181), the nucleic acid sample separation supplementary channel (133), the nucleic acid sample separation supplementary branch channel (131), the standard sample separation supplementary channel (143), and the standard sample separation supplementary branch channel (141), and 300 µm in case of the separation channel part (151). The length from the sample injection point to the separation channel part was 2 mm, and the total length of the separation channel part was 35 mm. Holes having the size of 2 mm were made at the ends of each microchannel, where storage parts were built using silicon tubing.

In order to form gels in microchannels except the certain parts (111 and 121) of the microchannels, an acrylamide solution containing a photoinitiator (a solution obtained by mixing 2% (w/v) Irgacure®651 (2,2-dimethoxy-1,2-diphenylethan-1-one) with 5% T(w/v) and 3.3% C(w/v) acrylamide solution dissolved in 1×TBE (trisborate-EDTA) so that its concentration became 6.7% (v/v)) was injected through the storage parts into all the microchannels, which were then exposed to a 350 W UV lamp (Osram, Germany) for 10 min. with the certain parts (111 and 121) of the microchannels being shielded using a mask. After exposure, the solutions that were not gelated were eliminated using a pressure difference. Thus, the manufactured microchip for nucleic acid separation and detection is as shown in FIG. 1A where each part is labeled, and the actual photograph of the microchip is shown in FIG. 1B with the pictures of the enlarged parts for sample injection.

Example 2

Analysis of Single Nucleic Acid Sample

In this example, the analysis ability of the microchip for nucleic acid separation and detection was tested by 1. injecting a nucleic acid sample and a standard sample, respectively, and analyzing them, and 2. by injecting a nucleic acid sample and a standard sample at the same time and analyzing them. For this, a DNA having the size of 323 bp amplified through a PCR process (a PCR product obtained by using a plasmid DNA (Promega, USA) isolated from bacteria kanamycin-resistant genes as a template DNA and using primers having the base sequences represented by SEQ. ID. No. 1 and SEQ. ID. No. 2 to amplify a fragment of 323 bp of the plasmid DNA) was used as a nucleic acid sample, standard size nucleic acids (DNA size markers, Promega, USA) containing DNAs having sizes of 50, 150, 300, 500, 750, and 1000 bps were used as standard samples, YOYO-1 (Molecular probes, USA) was used as a fluorescent dye, and 1×TBE was used as a buffer solution.

```
Forward primer for 323 bp:
                                    (SEQ. ID. No. 1)
5'-GCC ATT CTC ACC GGA TTC AGT CGTC-3', Reverse primer for 323 bp:
                                    (SEQ. ID. No. 2)
5'-AGC CGC CGT CCC GTC AAG TCAG-3'
```

PCR Conditions: Repeat the condition of 95° C. for 2 min., 95° C. for 30 sec., 60° C. for 1 min., and 72° C. for 2 min. 33 times, then leave at 72° C. for 5 min., and cool down to 4° C. to terminate the reaction (see KR2005-0078568).

First, as a step to prepare for conditions for analysis in the microchip, as seen in FIG. 2A, YOYO-1 was transferred toward the fluorescent dye discharge part (150) from the fluorescent dye storage part (160) through the separation channel part (151) by filling the fluorescent dye storage part (160) with YOYO-1, applying a voltage of −64.5 V/cm between the fluorescent dye discharge part (150) and the fluorescent dye storage part (160) for 30 min. to 50 min., and floating the buffer solution storage part for nucleic acid sample injection (170), the buffer solution storage part for standard sample injection (180), the buffer solution storage part for nucleic acid sample separation (130), and the buffer solution storage part for standard sample separation (140).

The introduction of the nucleic acid sample and the standard sample into the microchip as shown in FIG. 2B was carried out by the following three cases. First, in a case that only the 323 bp DNA sample was analyzed, the nucleic acid sample channel part (111) was filled with the 323 bp DNA and the standard sample channel part (121) was filled with the buffer solution. Second, in a case that only the standard sample (standard size nucleic acids) was analyzed, the standard sample channel part (121) was filled with the standard sample and the nucleic acid sample channel part (111) was filled with the buffer solution. Third, in a case that the nucleic acid sample and the standard sample were analyzed together, the nucleic acid sample channel part (111) was filled with the 323 bp DNA and the standard sample channel part (121) was filled with the standard size nucleic acids.

As shown in FIG. 2C, in order to inject a slight amount of nucleic acids of the nucleic acid sample to be used for analysis and detection and the standard size nucleic acids at the same time, each sample was injected into the nucleic acid sample separation supplementary channel (133) and the standard sample separation supplementary channel (143) by applying a voltage of −156.2 V/cm for 1 sec. between the buffer solution storage part for nucleic acid sample injection (170), the buffer solution storage part for standard sample injection (180), and the fluorescent dye storage part (160). Also, the buffer solution storage part for nucleic acid sample separation (130), the buffer solution storage part for standard sample separation (140), and the fluorescent dye discharge part (150)

were floated. In the first case in which only the nucleic acid sample was analyzed, the 323 bp DNA and the buffer solution were injected, in the second case in which only the standard sample was analyzed, the standard size nucleic acids and the buffer solution were injected, and in the third case in which the nucleic acid sample and the standard sample were analyzed together, the 323 bp DNA and the standard size nucleic acids were injected at the same time.

In order to transfer the slight amount of the injected nucleic acid sample (113) and the standard sample (123) to the separation channel part (151), as shown in FIG. 2D, a voltage of −86.2 V/cm was applied for 30 sec. to 1 min. between the buffer solution storage part for nucleic acid sample separation (130), the buffer solution storage part for standard sample separation (140), and the fluorescent dye storage part (160). Also, the buffer solution storage part for nucleic acid sample injection (170), the buffer solution storage part for standard sample injection (180), and the fluorescent dye discharge part (150) were floated.

Thereafter, in order to separate and detect the injected samples as shown in FIG. 2E, a voltage of −80.6 V/cm was applied for 3 min. to 5 min. between the fluorescent dye discharge part (150) and the fluorescent dye storage part (160). Also, the buffer solution storage part for nucleic acid sample injection (170), the buffer solution storage part for standard sample injection (180), the buffer solution storage part for nucleic acid sample separation (130), and the buffer solution storage part for standard sample separation (140) were floated. The slight amount of the nucleic acid sample (113) and the standard sample (123) injected into the separation channel part (151) traveled toward the fluorescent dye storage part (160) and were separated by their size. Here, the slight amount of the nucleic acid sample (113) and the standard sample (123) were coupled with YOYO-1 while passing through the separation channel part (151), and thus, by the irradiation of the fluorescence detection part (190) with a 488 nm argon ion laser (Lexel 95, Lexel Laser Inc, USA) as a light source, fluorescence signals from each of the samples separated by the size thereof were detected with a photomultiplier tube (H5784-01, Hamamatsu, USA).

In this example, the total amount of the nucleic acid sample was 5 μL, and of it, the slight amount of the nucleic acids to be injected into the separation channel part was 7 nL.

The voltages were regulated by a voltage divider, the source of voltage was a high voltage power supply (mp5, Spellman High Voltage Electronics, USA), and the Labview (National Instruments, USA) program and a multifunctional I/O board (National Instruments, USA) were employed to control them by a computer.

Figure 4:
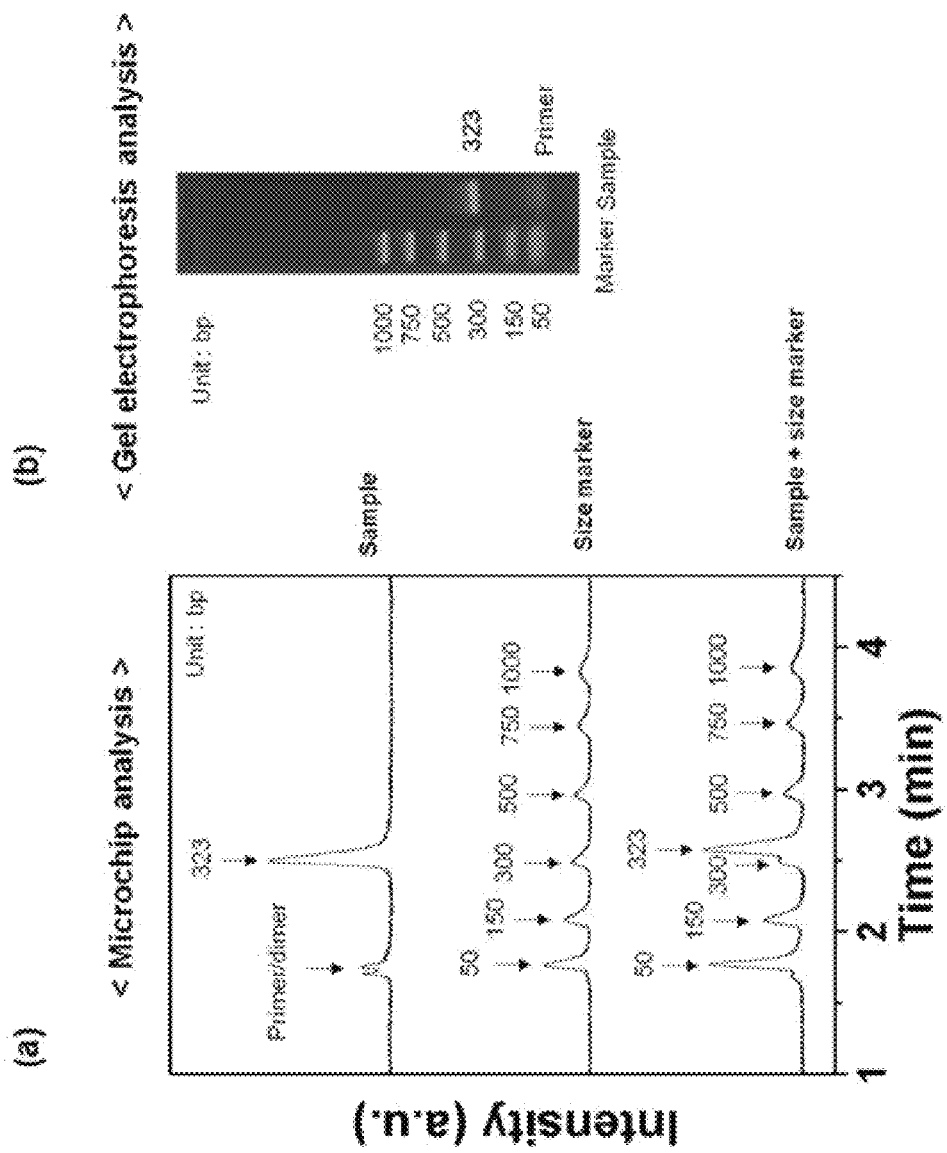
FIG. 4A and FIG. 4B are electropherograms showing respective nucleic acid sample separation, standard sample separation, and simultaneous separation of a nucleic acid sample and a standard sample according to the experimental example of the invention.

The separation results of the single nucleic acid sample and standard sample according to Example 2 of the invention are shown in FIG. 4. FIG. 4 (a) shows an electropherogram separated from the microchip, and FIG. 4 (b) is a picture of agarose gel electrophoresis showing the separation of the same samples. In FIG. 4 (a), the uppermost electropherogram shows the separation results of only the 323 bp nucleic acid sample, the middle electropherogram shows the separation results of the standard size nucleic acids which are the standard sample, and the lowermost electropherogram shows the separation results obtained by injecting the 323 bp which is the nucleic acid sample and the standard size nucleic acids which are the standard sample at the same time. FIG. 4 (b) shows the gel electrophoresis separation results obtained by inserting the standard size nucleic acids which are the standard sample into the left lane and inserting the 323 bp which is the nucleic acid sample into the right lane. It can be seen through the results of FIG. 4 that the separation ability of the microchip is as good as the ordinary gel electrophoresis method, and nucleic acid samples can be analyzed using much lesser amounts of the samples within a short time.

Example 3

Continuous Analysis for Multiple Nucleic Acid Samples and Checking Fluorescence Contamination In order to continuously analyze nucleic acid samples in the microchip, a high throughput device for performing continuous-flow reactions (Publication No. KR2005-0078568 A (Jong Hoon Hahn, Nokyoung Park, and Kwanseop Lim), Aug. 5, 2005) and the microchip for continuous nucleic acid separation and detection were connected to each other. The PCR was performed using the device for continuous-flow reactions, amplified DNAs having the three sizes of 323 bp, 640 bp, and 850 bp were sequentially injected into the microchip to analyze them in a continuous manner, and the three samples were collected to determine whether they were contaminated or not.

The 323 bp DNA (Promega) was obtained using a pair of primers as set forth in Example 2 above (see KR2005-007856).

As the 640 bp and the 850 bp, φx174RFI DNA (Accession No.: NC_001422) purchased from Takara was used, and pairs of primers used for each are as follows.

```
Forward primer for 640 bp:
                                 (SEQ. ID. No. 3)
5'-TCC GCT TTCC TCC TGA GAC-3'

Reverse primer for 640 bp:
                                 (SEQ. ID. No. 4)
5'-GGA AAC ACT GGT CAT AATC-3'

Forward primer for 850 bp:
                                 (SEQ. ID. No. 5)
5'-AGG CTC TAA TGT TCC TAA CCC TGA-3'

Reverse primer for 850 bp:
                                 (SEQ. ID. No. 6)
5'-TGA CGG TTA TTT CCT AGAC-3'
```

PCR Conditions: Repeat the condition of 95° C. for 2 min, 95° C. for 30 sec., 60° C. for 1 min., and 72° C. for 2 min. 33 times, then leave at 72° C. for 5 min., and cool down to 4° C. to terminate the reaction (see KR 2005-0078568).

The analysis procedure for multiple nucleic acid samples includes the analysis procedure for single nucleic acid sample in the above Example 2. As a fluorescent dye, buffer solution, and standard sample, the same kinds as in Example 2 were used, and each nucleic acid sample was injected simultaneously with the standard sample and then separated and detected. Specific procedures thereof are as follows.

As in Example 2, first, as a preparation step prior to sample analysis, YOYO-1 was transferred toward the fluorescent dye discharge part (150) from the fluorescent dye storage part (160) through the separation channel part (151) by filling the fluorescent dye storage part (160) with YOYO-1, applying a voltage of −64.5 V/cm between the fluorescent dye discharge part (150) and the fluorescent dye storage part (160) for 30 min. to 50 min., and floating the buffer solution storage part for nucleic acid sample injection (170), the buffer solution storage part for standard sample injection (180), the buffer solution storage part for nucleic acid sample separation (130), and the buffer solution storage part for standard sample separation (140), as shown in FIG. 2A.

Second, as shown in FIG. 2B, the standard size nucleic acids were filled into the standard sample channel part (121), and the nucleic acid sample was flowed to the nucleic acid sample channel part (111) by connecting the device for continuous-flow reactions (500) and the microchip for continuous nucleic acid detection (100). More particularly, the injection was performed in such a way that the sequence of the samples within the device for continuous-flow reactions (500) became carrier fluid—323 bp DNA in 5 μL—carrier fluid—washing solution—carrier fluid—640 bp DNA in 5 μL—carrier fluid—washing solution—carrier fluid—850 bp DNA in 5 μL, the samples were amplified under the above mentioned conditions in the device for continuous-flow reactions, and the amplified samples exited from the device of continuous-flow reactions and flowed to the nucleic acid sample discharge part (112) from the nucleic acid sample supply part (110) through the nucleic acid sample channel part (111).

The carrier fluids and the washing solutions inserted between the nucleic acid samples were injected to prevent a carry-over between the samples, and in particular, the carrier fluids are hydrophobic, which prevents the samples and the washing solutions which are hydrophilic from being mixed with each other, and the washing solutions serve to wash off the previous samples which might remain in Teflon tubes or microchannels when the samples flow in a continuous manner. In this example, 6× loading buffer (30% glycerol, 30 mM EDTA, 0.03% bromophenol blue, 0.03% xylene cyanol, Takara, Japan) was used as the washing solution, and perfluorodecalin (Acros Organics, Belgium) was used as the carrier fluid.

Third, when the first sample, 323 bp DNA, was passing through the nucleic acid sample channel part (111), the slight amount of 323 bp DNA which is the nucleic acid sample and the standard size nucleic acids which are the standard sample were injected into the nucleic acid sample separation supplementary channel (133) and the standard sample separation supplementary channel (143) by applying a voltage of −156.2 V/cm for 1 sec. between the buffer solution storage part for nucleic acid sample injection (170), the buffer solution storage part for standard sample injection (180), and the fluorescent dye storage part (160), and floating the buffer solution storage part for nucleic acid sample separation (130), the buffer solution storage part for standard sample separation (140), and the fluorescent dye discharge part (150), as in Example 2.

Fourth, in order to transfer the slight amount of the injected nucleic acid sample and the standard size nucleic acids to the separation channel part (151), a voltage of −86.2 V/cm was applied for 30 sec. to 1 min. between the buffer solution storage part for nucleic acid sample separation (130), the buffer solution storage part for standard sample separation (140), and the fluorescent dye storage part (160), and the buffer solution storage part for nucleic acid sample injection (170), the buffer solution storage part for standard sample injection (180), and the fluorescent dye discharge part (150) were floated, as in Example 2.

Fifth, in order to separate and detect the slight amount of the nucleic acid sample and the standard size nucleic acids having travelled to the separation channel part (151), the slight amount of 323 bp DNA and the standard size nucleic acids were separated at the same time by applying a separation voltage of −80.6 V/cm for 3 min. to 5 min. between the fluorescent dye discharge part (150) and the fluorescent dye storage part (160), and floating the buffer solution storage part for nucleic acid sample injection (170), the buffer solution storage part for standard sample injection (180), the buffer solution storage part for nucleic acid sample separation (130), and the buffer solution storage part for standard sample separation (140), as in Example 2. Further, by using a 488 nm argon ion laser (Lexel 95, Lexel Laser Inc, USA) as a light source at the fluorescence detection part (190) as in Example 2, fluorescence signals from the samples separated by the size thereof were detected with a photomultiplier tube (H5784-01, Hamamatsu, USA).

Sixth, when a washing solution (6× loading buffer) added prior to the second 640 bp sample was passing through the nucleic acid sample channel part (111) after the analysis of the first 323 bp DNA sample, the 6× loading buffer was injected into the nucleic acid sample separation supplementary channel (133) by applying a voltage of −156.2 V/cm for 3 sec. between the buffer solution storage part for nucleic acid sample injection (170) and the fluorescent dye storage part (160), and floating the buffer solution storage part for standard sample injection (180), the buffer solution storage part for nucleic acid sample separation (130), the buffer solution storage part for standard sample separation (140), and the fluorescent dye discharge part (150). This procedure is to prevent the carry-over between the samples by eliminating the first sample using a 6× loading buffer since the first sample might remain in the nucleic acid sample separation supplementary channel (133) prior to the analysis of the second nucleic acid sample. Thereafter, in order to eliminate the injected 6× loading buffer and the nucleic acid sample and the standard sample which might remain in the microchannels, the injected 6× loading buffer was transferred to the separation channel part by applying a voltage of −86.2 V/cm for 30 sec. to 1 min. between the buffer solution storage part for nucleic acid sample separation (130), the buffer solution storage part for standard sample separation (140), and the fluorescent dye storage part (160), and floating the buffer solution storage part for nucleic acid sample injection (170), the buffer solution storage part for standard sample injection (180), and the fluorescent dye discharge part (150).

Then, the 6× loading buffer injected into the separation channel part (151) was discharged toward the fluorescent dye storage part (160) by applying a separation voltage of −80.6 V/cm for 3 min. to 5 min. between the fluorescent dye discharge part (150) and the fluorescent dye storage part (160), and floating the buffer solution storage part for nucleic acid sample injection (170), the buffer solution storage part for standard sample injection (180), the buffer solution storage part for nucleic acid sample separation (130), and the buffer solution storage part for standard sample separation (140).

With regard to the 640 bp DNA sample following the 323 bp DNA, the third procedure to the sixth procedure of above Example 3 were performed, wherein when the 640 bp DNA was passing through the nucleic acid sample channel part (111), the slight amount of the 640 bp DNA and the standard size sample were injected at the same time, and then, after separation and detection, it went through with the step to prevent the carry-over between the samples.

With regard to the final third nucleic acid 850 bp DNA sample, the third procedure to the fifth procedure of above Example 3 proceeded without the washing procedure since there was no following sample, to perform sample injection, separation, and detection. In such a way, the nucleic acid samples having the sizes of 323 bp, 640 bp, and 850 bp were able to be analyzed in a continuous manner.

FIG. 5A shows the connection of the device for continuous-flow reactions and the microchip for continuous nucleic acid separation and detection according to Example 3 of the present invention, wherein the discharge part of the device for continuous-flow reactions (500) is connected to the nucleic acid sample supply part (110) of the microchip for continuous nucleic acid separation and detection (100) so that each nucleic acid amplified in the device for continuous-flow reactions (500) passes through the nucleic acid sample channel part (111) from the nucleic acid sample supply part (110) and sequentially exits from the nucleic acid sample discharge part (112), and it shows that the size of nucleic acids are analyzed and the samples are collected.

Figure 5B:
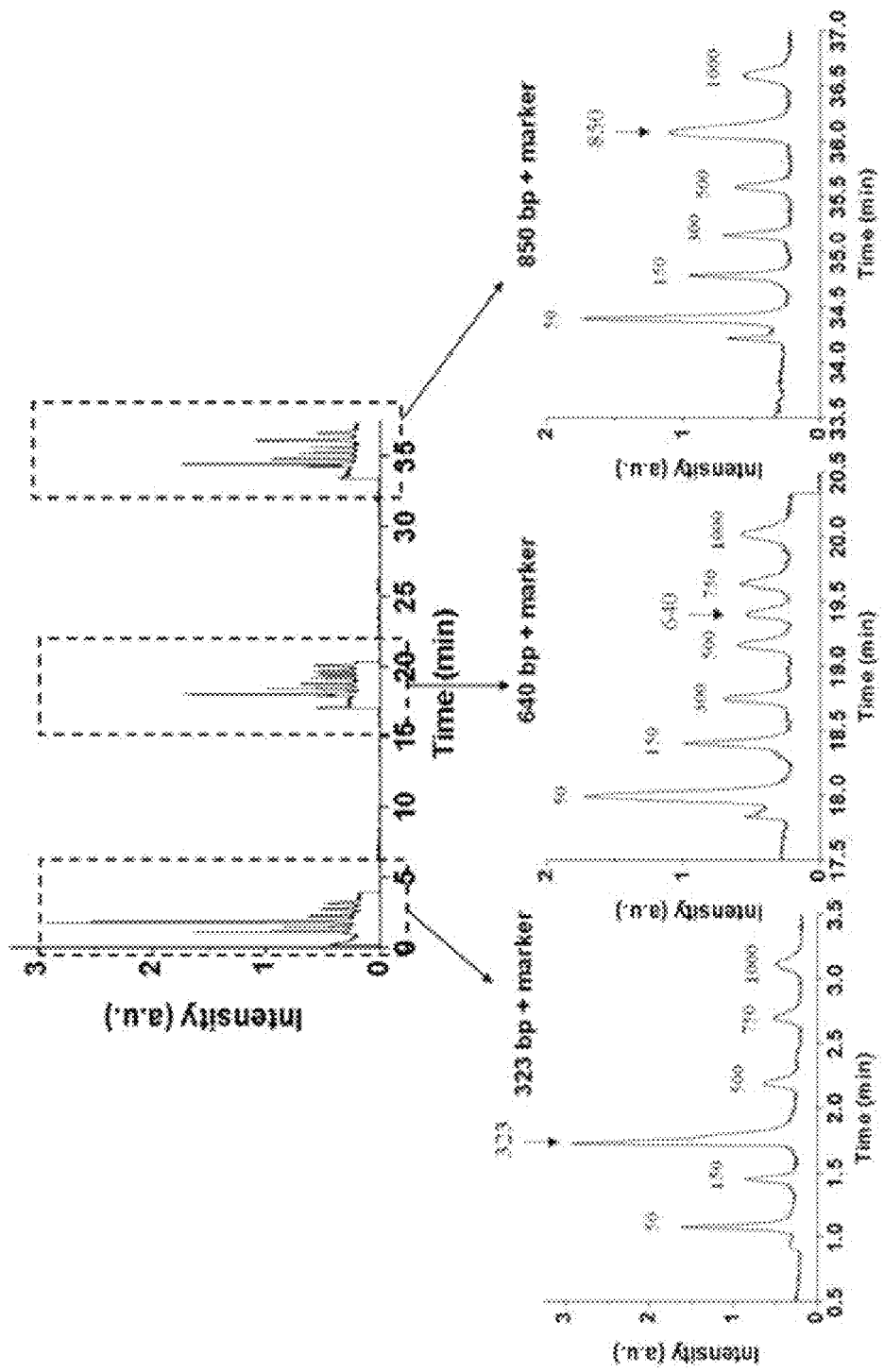
FIG. 5B shows electropherograms of continuous detection of three nucleic acid samples and standard size nucleic acids, and enlarged electropherograms of each sample.

FIG. 5B shows an electropherogram obtained by analyzing the nucleic acid samples having the sizes of 323 bp, 640 bp, and 850 bp along with the standard size nucleic acids in a continuous manner by the methods described above. The nucleic acid sample and the standard size nucleic acids were separated by the size thereof, and a nucleic acid having a smaller size started to appear in order in the electropherogram. In the case of the first 323 bp sample, as it was injected along with the standard size nucleic acids of 50 bp, 150 bp, 300 bp, 500 bp, 750 bp, and 1000 bp, the signal of the 323 bp nucleic acids appeared between the standard size nucleic acids 150 bp and 500 bp. In the case of the 323 bp, as it had little difference from the standard size 300 bp nucleic acids and its amount was relatively huge, their signals were overlapped. The second 640 bp sample showed its signal between the standard size nucleic acids 500 bp and 750 bp, and the third 850 bp sample was overlapped with 750 bp between 500 bp and 1000 bp because it was present in a relatively huge amount. The time for which each nucleic acid sample was separated was within 3 min., and it showed no carry-over between the samples by virtue of the injection of a washing solution after the separation of a sample.

Each sample passing through the nucleic acid sample channel part (111) was collected through tubing for sample collection (220), and the fluorescence signal was measured from the samples with a fluorescence spectrometer (Cary Eclipse Fluorescence Spectrophotometer, Varian, Australia). For the comparison of fluorescence signals, 323 bp DNA and YOYO-1 as a positive control were mixed in a mole ratio of 12:1, and its fluorescence intensity was measured. In comparison with the fluorescence intensities of the samples, it was confirmed that the samples exhibited no fluorescence.

Figure 6:
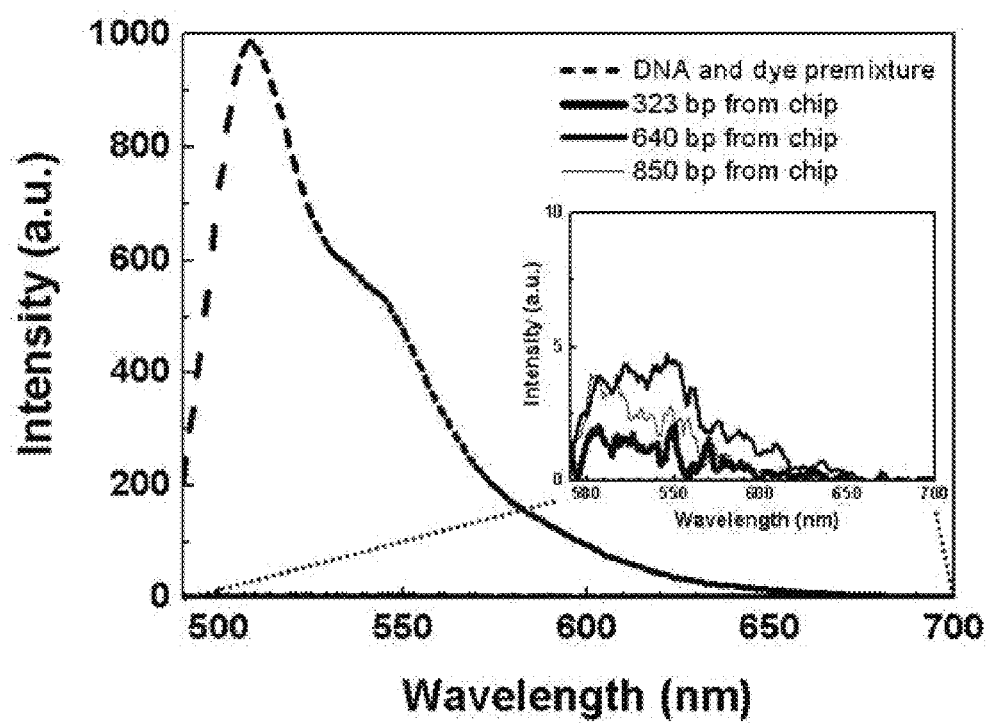
FIG. 6 shows the results of checking fluorescence dye contamination obtained by measuring the fluorescence values of the three nucleic acid samples collected after the continuous analysis thereof according to the experimental example of the invention, by a fluorescence spectrometer.

The results are shown in FIG. 6. FIG. 6 shows the results obtained by measuring, with a fluorescence spectrometer, the fluorescence values from each sample collected after the continuous separation of nucleic acid samples according to Example 3 of the present invention and the positive control, and since each collected sample exhibited no fluorescence when compared with the positive control, it was confirmed that there was no contamination with fluorescent dyes.

While the invention has been described with respect to the specific embodiments thereof in the detailed description of the invention, it should be understood that various modifications can be made within the scope of the invention. Therefore, the scope of the invention is not restricted to the described embodiments, and it should be defined by not only the appended claims but also by equivalents thereof.

DESCRIPTION OF REFERENCE NUMERALS

100: microchip for continuous nucleic acid separation and detection
110: nucleic acid sample supply part
111: nucleic acid sample channel part
112: nucleic acid sample discharge part
113: slight amount of the nucleic acid sample
120: standard sample supply part
121: standard sample channel part
122: standard sample discharge part
123: standard sample
130: buffer solution storage part for nucleic acid sample separation
140: buffer solution storage part for standard sample separation
131: nucleic acid separation supplementary branch channel
133: nucleic acid separation supplementary channel
141: standard sample separation supplementary branch channel
143: standard sample separation supplementary channel
150: fluorescent dye discharge part
151: separation channel part
160: fluorescent dye storage part
170: buffer solution storage part for nucleic acid sample injection
180: buffer solution storage part for standard sample injection
171: nucleic acid sample injection supplementary channel
181: standard sample injection supplementary channel
190: light detection part
200, 210: tubing for sample injection
220, 230: tubing for sample collection
300, 310, 320, 330, 340, and 350: electrodes
410: light source part                420: optical lens
430: filter                           440: detector
450: data processor
500: device for continuous-flow reactions

What is claimed is:

1. A method for nucleic acid analysis, using a microchip comprising a nucleic acid sample channel part comprising a nucleic acid sample supply part and a nucleic acid sample discharge part, a standard sample channel part comprising a standard sample supply part and a standard sample discharge part, a separation channel part comprising a fluorescent dye storage part and a fluorescent discharge part at its both ends, a nucleic acid sample separation supplementary channel connecting the nucleic acid sample channel part and the separation channel part, and a standard sample separation supplementary channel connecting the standard sample channel part and the separation channel part, wherein the channels except the nucleic acid sample channel part and the standard sample channel part are filled with a polymer gel, comprising:

(1) supplying a nucleic acid sample through the nucleic acid sample supply part, so that the supplied nucleic acid sample flows toward the nucleic acid sample discharge part;

(2) supplying a standard size nucleic acid as a standard sample through the standard sample supply part;

(3) injecting a slight volume of the nucleic acid sample which flows in the nucleic acid sample channel part into the separation channel part through the nucleic acid sample separation supplementary channel by applying a negative voltage for 0.1 to 2 seconds to an end of a nucleic acid sample injection supplementary channel that is extended from a connection part which is a point at which the nucleic acid sample channel part and the nucleic acid sample separation supplementary channel are connected;

(4) injecting the standard sample into the separation channel part through the standard sample separation supplementary channel by applying a negative voltage for 0.1 to 2 seconds to an end of a standard sample injection supplementary channel extended from a connection part which is a point at which the standard sample channel part and the standard sample separation supplementary channel are connected;

(5) reacting the fluorescent dye with the nucleic acid sample and the standard sample by applying a negative voltage to a fluorescent sample discharge part of the separation channel part, allowing a fluorescent dye having a positive charge to transfer to the fluorescent sample discharge part and to transfer the nucleic acid sample and the standard sample injected into the separation channel part in a direction opposite to the fluorescent sample discharge part; and (6) separating the nucleic acid sample and the standard sample reacted with the fluorescent dye in the separation channel part and conducting fluorescence detection wherein the slight volume of the nucleic acid sample is in the range of 0.1 pL to 10 nL.

2. The method for nucleic acid analysis of claim 1, wherein the nucleic acid sample separation supplementary channel of the microchip for analyzing nucleic acid further comprises a nucleic acid sample separation supplementary branch channel branched between the separation channel part and the nucleic acid sample channel part, and the standard sample separation supplementary channel further comprises a standard sample separation supplementary branch channel branched between the separation channel part and the standard sample channel part, and the method for nucleic acid analysis further comprises a step (3-1) of removing a fluorescent dye exited from the separation channel part to the nucleic acid sample separation supplementary channel by applying a negative voltage to an end of the nucleic acid sample separation supplementary branch channel, simultaneously with or subsequently to the step (3), and a step (4-1) of removing a fluorescent dye exited from the separation channel part to the standard sample separation supplementary channel by applying a negative voltage to an end of the standard sample separation supplementary branch channel, simultaneously with or subsequently to the step (4).

3. The method for nucleic acid analysis of claim 2, wherein the microchip for analyzing nucleic acid further comprises a buffer solution storage part for nucleic acid sample injection and a buffer solution storage part for standard sample injection at an end of the nucleic acid sample injection supplementary channel and at an end of the standard sample injection supplementary channel, respectively, and a buffer solution storage part for nucleic acid sample separation and a buffer solution storage part for standard sample separation at an end of the nucleic acid sample separation supplementary branch channel and the standard sample separation supplementary branch channel, respectively, and a step of preparing the separation channel part comprising a fluorescent dye having a positive charge is conducted prior to the step (1) and step (2), or prior to the step (3) and step (4), by performing the steps of:

(a) applying a negative voltage to the fluorescent dye discharge part of the separation channel part;

(b) floating the buffer solution storage part for nucleic acid sample injection, the buffer solution storage part for standard sample injection, the buffer solution storage part for nucleic acid sample separation, the buffer solution storage part for standard sample separation, or the fluorescent dye discharge part; and (c) pre-running a fluorescent dye or a buffer solution for 5 to 90 minutes by grounding the fluorescent dye storage part.

4. The method for nucleic acid analysis of claim 3, wherein the steps (3) and (4) are performed by:

i) simultaneously applying a negative voltage to the buffer solution storage part for nucleic acid sample injection and the buffer solution storage part for standard sample injection;

ii) floating the buffer solution storage part for nucleic acid sample separation, the buffer solution storage part for standard sample separation, and the fluorescent dye discharge part; and iii) grounding the fluorescent dye storage part.

5. The method for nucleic acid analysis of claim 4, wherein the step (3-1) and the step (4-1) comprise, subsequent to the steps (i) and (iii):

simultaneously applying a negative voltage to the buffer solution storage part for nucleic acid sample separation and the buffer solution storage part for standard sample separation;

floating the buffer solution storage part for nucleic acid sample injection, the buffer solution storage part for standard sample injection, and the fluorescent dye discharge part; and grounding the fluorescent dye storage part.

6. The method for nucleic acid analysis of claim 1, wherein the nucleic acid sample, excluding the slight volume of the nucleic acid sample to be injected into the separation channel part, of the nucleic acid sample supplied through the nucleic acid sample supply part, is collected without being contaminated with the fluorescent dye.

7. The method for nucleic acid analysis of claim 1, wherein the standard size nucleic acid is DNA in the range of 50 bp to 10 kbp.

8. The method for nucleic acid analysis of claim 1, wherein the step of separating the nucleic acid sample and the standard sample reacted with the fluorescent dye in the separation channel part and conducting fluorescence detection is performed by connecting a light source for inducing fluorescence at a part near the fluorescent dye storage part of the separation channel part, a detector for detecting fluorescence, and an optical device for collecting the generated fluorescence to the detector, and detecting fluorescence.

9. The method for nucleic acid analysis of claim 8, wherein the light source is selected from the group consisting of a light emitting device, a laser, and a UV lamp.

10. The method for nucleic acid analysis of claim 1, wherein the fluorescent dye is one or more selected from the group consisting of an intercalating dye which specifically binds to a double-stranded nucleic acid to emit fluorescence, and a fluorescent dye having a positive charge.

11. The method for nucleic acid analysis of claim 10, wherein:

the intercalating dye is one or more selected from the group consisting of EtBr, POPO, SYBR Green, Pico Green, YOYO, and TOTO; and the fluorescent dye having a positive charge is one or more selected from the group consisting of DAPI (2-(4-carbamimidoylphenyl)-1H-indole-6-carboximidamide, $C_{16}H_{15}N_5$) and Hoechst 33258 (4-[5-[6-(4-methylpiperazin-1-yl)-1H-benzimidazol-2-yl]-1,3-dihydrobenzimidazol-2-ylidene]cyclohexa-2,5-dien-1-one, $C_{25}H_{24}N_6O$).

12. The method for nucleic acid analysis of claim 1, wherein the nucleic acid sample is selected from the group consisting of DNA (deoxyribonucleic acid), RNA (ribonucleic acid), and cDNA (complimentary DNA).

13. The method for nucleic acid analysis of claim 12, wherein the nucleic acid sample is an amplified product of a PCR (polymerase chain reaction).

14. The method for nucleic acid analysis of claim 1, wherein the nucleic acid sample supply part is connected with a pump for sample transport, or a nucleic acid amplification device.

15. The method for nucleic acid analysis of claim 1, wherein the step of supplying the nucleic acid sample into the nucleic acid sample channel part through the nucleic acid sample supply part comprises a step of sequentially introducing nucleic acid samples that are different from each other, to separate the different nucleic acid samples in a continuous manner.

16. The method for nucleic acid analysis of claim 15, wherein the step of sequentially introducing nucleic acid samples that are different from each other comprises a step of connecting the nucleic acid sample supply part with a pump for sample transport containing different nucleic acid samples, or with a continuous nucleic acid amplification device, to sequentially introduce the nucleic acid samples.

17. The method for nucleic acid analysis of claim 16, wherein each nucleic acid of the different nucleic acid samples introduced by being connected to the pump for sample transport or the nucleic acid amplification device is placed between carrier fluids and transferred to the nucleic acid sample channel part, and the carrier fluids are not mixable with water.

18. The method for nucleic acid analysis of claim 15, wherein simultaneously with or subsequently to the step (6) of separating and detecting the slight volume of the nucleic acid sample and the standard sample injected into the separation channel part by fluorescence, a step (1) of introducing a different nucleic acid sample through the nucleic acid sample supply part and the following steps (2), (3), (4), (5), and (6) or steps (3), (4), (5), and (6) are repeatedly performed.

19. A microchip for analyzing nucleic acid, using the method of claim 1 comprising:
  a nucleic acid sample channel part which is connected with a nucleic acid sample supply part and a nucleic acid sample discharge part to allow continuous flow of a fluid from the nucleic acid sample supply part to the nucleic acid sample discharge part;
  a standard sample channel part which is connected with a standard sample supply part and a standard sample discharge part;
  a separation channel part which is located between the nucleic acid sample channel part and the standard sample channel part, one end of which a fluorescent dye storage part is connected to, and the other end of which a fluorescent dye discharge part is connected to;
  a nucleic acid sample separation supplementary channel connecting the nucleic acid sample channel part and the separation channel part;
  a standard sample separation supplementary channel connecting the standard sample channel part and the separation channel part;
  a nucleic acid sample injection supplementary channel extended from a connection part which is a point at which the nucleic acid sample channel part is connected with the nucleic acid sample separation supplementary channel; and
  a standard sample injection supplementary channel extended from a connection part which is a point at which the standard sample channel part is connected with the standard sample separation supplementary channel,
  wherein the separation channel part, the nucleic acid sample separation supplementary channel, the standard sample separation supplementary channel, the nucleic acid sample injection supplementary channel, and the standard sample injection supplementary channel are filled with a polymer gel, and
  an electrode is formed at the fluorescent dye discharge part, the fluorescent dye storage part, an end of the nucleic acid sample injection supplementary channel, and an end of the standard sample injection supplementary channel.

20. The microchip for analyzing nucleic acid of claim 19, wherein the nucleic acid sample separation supplementary channel further comprises a nucleic acid sample separation supplementary branch channel branched between the separation channel part and the nucleic acid sample channel part,
  the standard sample separation supplementary channel further comprises a standard sample separation supplementary branch channel branched between the separation channel part and the standard sample channel part,
  the separation supplementary branch channels are each filled with a polymer gel, and
  an electrode is formed at an end of each of the separation supplementary branch channels.

21. The microchip for analyzing nucleic acid of claim 20, further comprising a buffer solution storage part for nucleic acid sample separation and a buffer solution storage part for standard sample separation in the electrode region at the end of the nucleic acid sample separation supplementary branch channel and the standard sample separation supplementary branch channel, respectively.

22. The microchip for analyzing nucleic acid of claim 19, wherein the electrode is formed from one or more materials selected from the group consisting of gold, silver, platinum, copper, aluminum, and indium tin oxide (ITO).

23. The microchip for analyzing nucleic acid of claim 19, wherein the polymer gel is in a solution state in which a polymer selected from the group consisting of polyacrylamide gel, hydroxyalkyl cellulose, polyvinyl alcohol, and dextran is mixed with a buffer solution.

24. The microchip for analyzing nucleic acid of claim 19, further comprising a buffer solution storage part for nucleic acid sample injection and a buffer solution storage part for standard sample injection in the electrode region at the end of the nucleic acid sample injection supplementary branch channel and the standard sample injection supplementary branch channel, respectively.

25. The microchip for analyzing nucleic acid of claim 19, further comprising a light source for inducing fluorescence at a part near the fluorescent dye storage part of the separation channel part, a detector for detecting fluorescence, and an optical device for collecting the generated fluorescence to the detector.

26. The microchip for analyzing nucleic acid of any one of claims 19 to 25, wherein the nucleic acid sample supply part is connected with a pump for sample transport or a nucleic acid amplification device.

27. The microchip for analyzing nucleic acid of claim 26, wherein the pump for sample transport or the nucleic acid amplification device is used to transport nucleic acids from each other or to produce amplified nucleic acid products that are different from each other.

\* \* \* \* \*